United States Patent
Park et al.

(10) Patent No.: US 8,367,219 B2
(45) Date of Patent: *Feb. 5, 2013

(54) ANTHRACENE-BASED COMPOUND AND ORGANIC LIGHT EMITTING DEVICE EMPLOYING THE SAME

(75) Inventors: Sang-hoon Park, Yongin-si (KR); O-hyun Kwon, Yongin-si (KR); Seung-gak Yang, Yongin-si (KR); Yu-jin Kim, Yongin-si (KR); Yu-ri Choi, Yongin-si (KR)

(73) Assignees: Samsung Electronics Co., Ltd., Yeongtong-gu, Suwon-si, Gyeonggi-do (KR); Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 302 days.

This patent is subject to a terminal disclaimer.

(21) Appl. No.: 12/285,090

(22) Filed: Sep. 29, 2008

(65) Prior Publication Data

US 2009/0108746 A1 Apr. 30, 2009

(30) Foreign Application Priority Data

Oct. 30, 2007 (KR) .......................... 10-2007-0109731
Apr. 28, 2008 (KR) .......................... 10-2008-0039348

(51) Int. Cl.
*H01L 51/54* (2006.01)
*C09K 11/06* (2006.01)

(52) U.S. Cl. ........ 428/690; 428/917; 313/502; 313/504; 546/144

(58) Field of Classification Search .................... None
See application file for complete search history.

(56) References Cited

U.S. PATENT DOCUMENTS

| 4,885,211 A | 12/1989 | Tang et al. | |
|---|---|---|---|
| 5,151,629 A | 9/1992 | VanSlyke | |
| 6,824,895 B1 * | 11/2004 | Sowinski et al. | 428/690 |
| 2006/0154105 A1 * | 7/2006 | Yamamoto et al. | 428/690 |
| 2008/0111473 A1 | 5/2008 | Kawamura et al. | |

FOREIGN PATENT DOCUMENTS

| CN | 1751024 | 3/2006 |
|---|---|---|
| CN | 101087759 | 12/2007 |
| EP | 1 582 516 | 10/2005 |
| EP | 1582516 | 10/2005 |
| EP | 1 734 038 | 12/2006 |
| JP | 2003-123983 | 4/2003 |
| WO | 2004/075603 | 9/2004 |
| WO | 2004/075604 | 9/2004 |
| WO | 2006/067931 A1 | 6/2006 |
| WO | WO 2006/067931 A1 * | 6/2006 |
| WO | 2007/029696 | 3/2007 |
| WO | WO 2007/026847 | 3/2007 |

OTHER PUBLICATIONS

Search Report from the European Patent Office issued in Applicant's corresponding European Patent Application No. 08167627.2 on Feb. 23, 2009.
Examination Report issued by the European Patent Office on Jul. 26, 2010 for a corresponding European Patent Application No. 08167627.2.
European Examination Report issued by EPO on Aug. 11, 2011 in connection with European Patent Application No. 08167627.2, which also claims Korean Patent Applications No. 10-2007-0109731 and No. 10-2008-0039348 as its priority documents.
Chinese Office Action issued Sep. 11, 2012 in connection with Chinese Patent Application Serial No. 200910132198.8, which also claims Korean Patent Application Serial No. 10-2008-0039348 as a priority document, and its partial English translation attached herewith.

* cited by examiner

*Primary Examiner* — Lynda Salvatore
*Assistant Examiner* — Andrew K Bohaty
(74) *Attorney, Agent, or Firm* — Robert E. Bushnell, Esq.

(57) ABSTRACT

Provided are an anthracene-based compound represented by Formula 1 or 2 and an organic light emitting device employing the same:

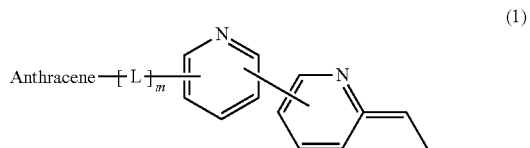

(1)

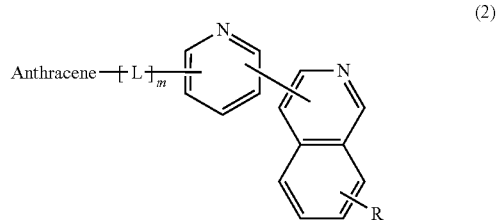

(2)

where R is a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group or a substituted or unsubstituted C2-C30 heteroaryl group, L is a bivalent linking group and a substituted or unsubstituted C6-C30 arylene group or a substituted or unsubstituted C2-C30 heteroarylene group, and m is an integer of 0 to 3.

16 Claims, 6 Drawing Sheets

ANTHRACENE-BASED COMPOUND AND ORGANIC LIGHT EMITTING DEVICE EMPLOYING THE SAME

CROSS-REFERENCE TO RELATED PATENT APPLICATION AND CLAIM OF PRIORITY

This application claims the benefit of Korean Patent Application Nos. 10-2007-0109731, filed on Oct. 30, 2007 and 10-2008-0039348, filed on Apr. 28, 2008, in the Korean Intellectual Property Office, the disclosure of which is incorporated herein in its entirety by reference.

BACKGROUND OF THE INVENTION

1. Field of the Invention

The present invention relates to an anthracene-based compound and an organic light emitting device employing the same, and more particularly, to an anthracene-based compound including a pyridinylquinoline-based group or a pyridinylisoquinoline-based group and an organic light emitting device including an organic layer formed of the anthracene-based compound.

2. Description of the Related Art

Organic light emitting devices are active light emitting display devices that emit light by recombination of electrons and holes in a thin layer made of a fluorescent or phosphorescent organic compound (an organic layer) when a current is applied to the organic layer. The organic light emitting devices have advantages such as lightweight, simple constitutional elements, an easy fabrication process, superior image quality and a wide viewing angle. Furthermore, the organic light emitting devices can accomplish perfect creation of dynamic images and high color purity. The organic light emitting devices also have electrical properties, such as low power consumption and low driving voltage, suitable for portable electronic equipment A multi-layered organic light emitting device using an aluminum quinolinol complex layer and a triphenylamine derivative layer was developed by Eastman Kodak Co. (U.S. Pat. No. 4,885,211), and a wide range of light from ultraviolet lights to infrared lights can be emitted using low-molecular weight materials when an organic emitting layer is formed (U.S. Pat. No. 5,151,629).

Light emitting devices, which are self light emitting display devices, have wide viewing angles, excellent contrast and a quick response. Light emitting devices are classified into inorganic light emitting devices using inorganic compounds to form emitting layers and organic light emitting devices (OLED) using organic compounds to form emitting layers. Organic light emitting devices have higher brightness, lower driving voltages and quicker responses than inorganic light emitting devices and can realize multi colors. Thus, organic light emitting devices have been actively studied.

Typically, an organic light emitting device has an anode/organic emitting layer/cathode structure. An organic light emitting device can also have various other structures, such as an anode/hole injection layer/hole transport layer/emitting layer/electron transport layer/electron injection layer/cathode structure or an anode/hole injection layer/hole transport layer/emitting layer/hole blocking layer/electron transport layer/electron injection layer/cathode structure.

Materials that are used in organic light emitting devices can be classified into vacuum deposited materials and solution coated materials according to a method of preparing an organic layer. The vacuum deposited materials may have a vapor pressure of $10^{-6}$ torr or greater at the temperature of 500° C. or less and may be low molecular materials having a molecular weight of 1200 or less. The solution coated materials may be highly soluble in solvents to be prepared in solution phase, and include aromatic or heterocyclic groups.

When an organic light emitting device is manufactured by vacuum deposition, costs may be increased due to expensive vacuum systems and high resolution pixels may not be easily manufactured if a shadow mask is used to prepare pixels for a natural color display. On the other hand, an organic light emitting device can be easily and inexpensively manufactured using solution coating such as inkjet printing, screen printing and spin coating and can have relatively high resolution compared to when using a shadow mask.

Meanwhile, when a conventional organic light emitting device is operated or stored at a high temperature, emitting light may be changed, light emitting efficiency may be reduced, driving voltages may be increased, and lifetime may be shortened. In order to prevent those problems, a novel electron transport material having a high glass transition temperature (Tg) and capable of reducing driving voltage needs to be developed.

Oxadiazole derivatives, triazole derivatives, phenanthroline derivatives and aluminum complexes are widely used as an electron transport material. In particular, research on an electron transport material using a phenanthroline-based or bipyridine-based compound is vigorously performed.

International Publication No. WO2007/026847 discloses a compound having a triazole ring structure substituted with a pyridyl group, and Japanese Patent Publication No. hei 15-123983 discloses a 1,10-phenanthroline-based compound to manufacture organic light emitting devices having low driving voltage and high efficiency by using higher electron transporting capability compared to conventional electron transport materials.

SUMMARY OF THE INVENTION

According to an aspect of the present invention, there is provided an anthracene-based compound comprising a compound represented by Formula 1 or 2 below:

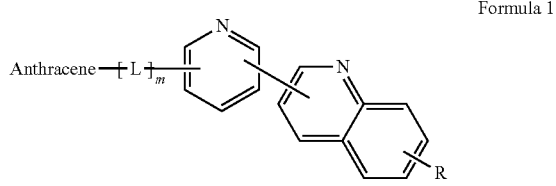

Formula 1

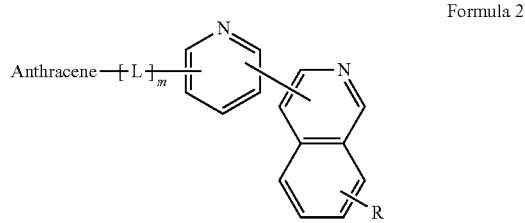

Formula 2 wherein R is selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group, L is a bivalent linking group and a substituted or unsubstituted C6-C30 arylene group or a substituted or unsubstituted C2-C30 heteroarylene group, and m is an integer of 0 to 3.

According to another aspect of the present invention, there is provided an organic light emitting device comprising:

a first electrode;

a second electrode; and at least one organic layer between the first electrode and the second electrode, wherein the organic layer comprises the anthracene-based compound.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1A:
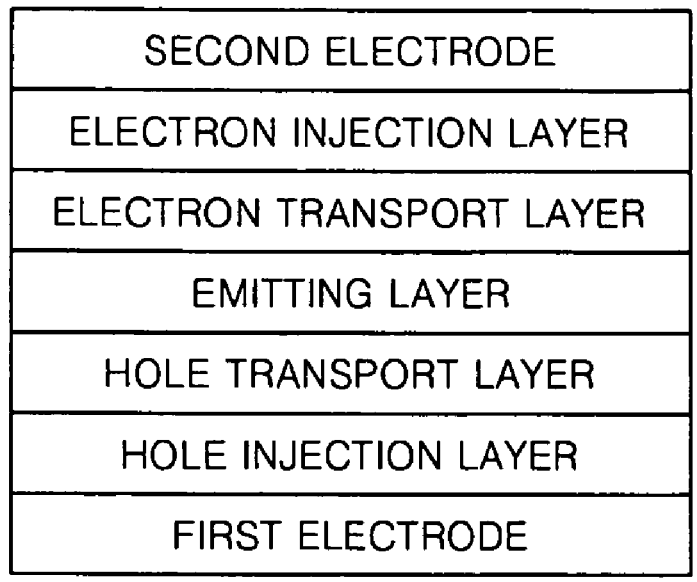
FIG. 1A is a schematic sectional view of an organic light emitting device according to an embodiment of the present invention.

Hereinafter, the present invention will now be described more fully with reference to the accompanying drawings, in which exemplary embodiments of the invention are shown.

According to an embodiment of the present invention, an anthracene-based compound represented by Formula 1 or 2, i.e., anthracene having a pyridinylquinoline-based group or a pyridinylisoquinoline-based group.

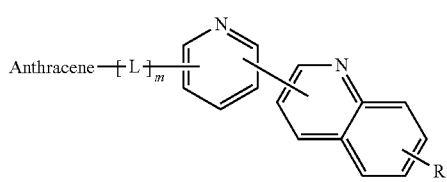

Formula 1

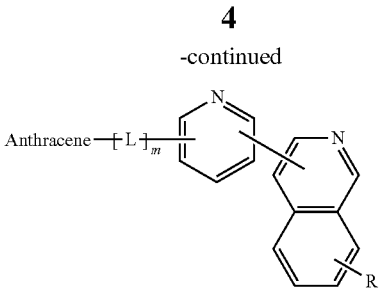

Formula 2

In Formula 1 or 2, R is a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group or a substituted or unsubstituted C2-C30 heteroaryl group;

L is a bivalent linking group and a substituted or unsubstituted C6-C30 arylene group or a substituted or unsubstituted C2-C30 heteroarylene group; and m is 0, 1, 2 or 3.

In Formula 1 or 2, a hydrogen atom of the "Anthracene" is substituted with the pyridinylquinoline-based group or the pyridinylisoquinoline-based group, and the other hydrogens of the "Anthracene" may be substituted or unsubstituted.

Here, the position of the carbons of anthracene is numbered as follows.

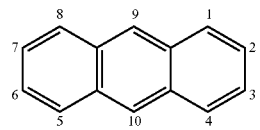

In the anthracene-based compound according to an embodiment of the present invention, the hydrogen of the "Anthracene" in Formula 1 or 2 may be substituted with the pyridinylquinoline-based group or the pyridinylisoquinoline-based group in one of the positions selected from the group consisting of C2, C3, C6, C7, C9 and C10 positions of anthracene.

The anthracene-based compound may be represented by one of Formulae 3 to 6 below:

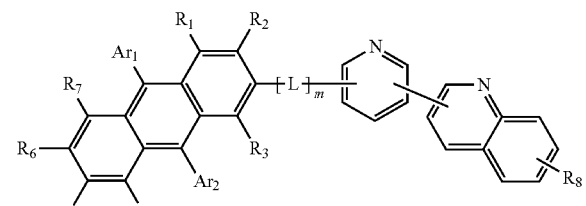

Formula 3

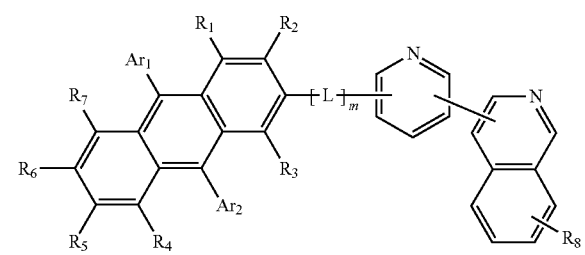

Formula 4

-continued

Formula 5

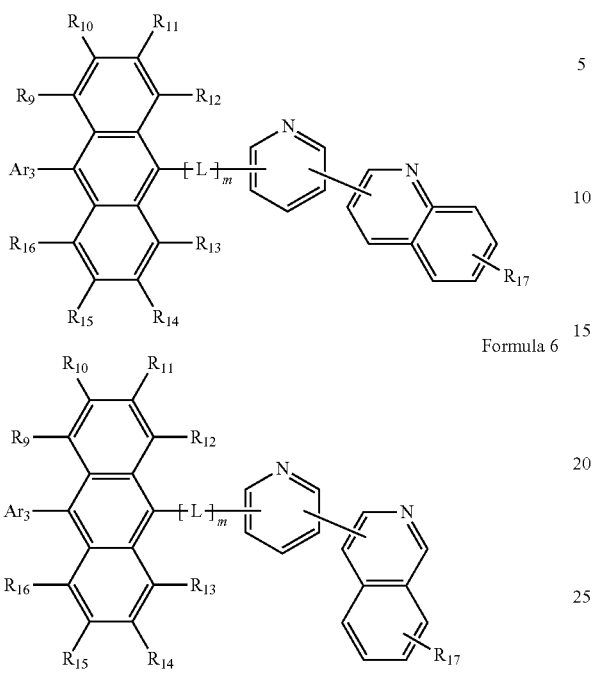

Formula 6

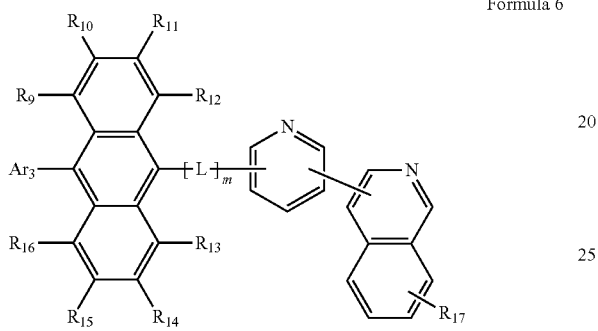

wherein $R_1$ to $R_{17}$ are identical to or different from each other and each independently one selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group;

$Ar_1$, $Ar_2$ and $Ar_3$ are identical to or different from each other and are each independently a substituted or unsubstituted C6-C30 aryl group;

L is a bivalent linking group, and L is a substituted or unsubstituted C6-C30 arylene group or a substituted or unsubstituted C2-C30 heteroarylene group; and m is 0, 1, 2 or 3.

For example, in Formulae 3 to 6, L is independently one of the bivalent linking group and may be represented by formulae A-1 through A-21 below:

[A-1]
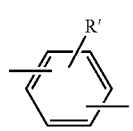

[A-2]
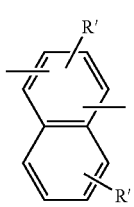

[A-3]
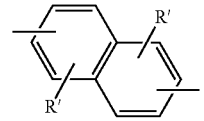

[A-4]
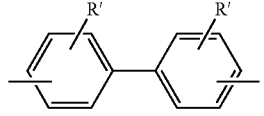

[A-5]
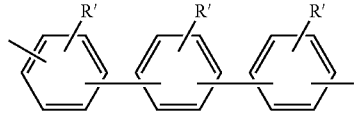

[A-6]
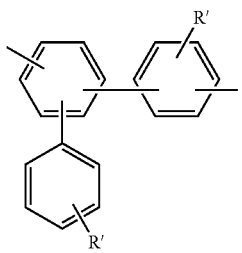

[A-7]
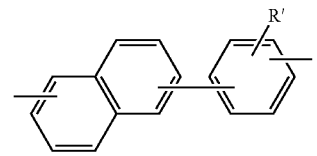

[A-8]
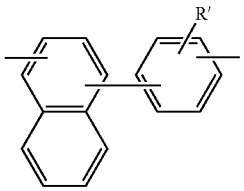

[A-9]
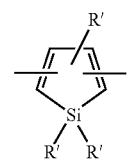

[A-10]
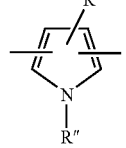

[A-11]
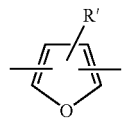

[A-12]
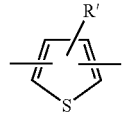

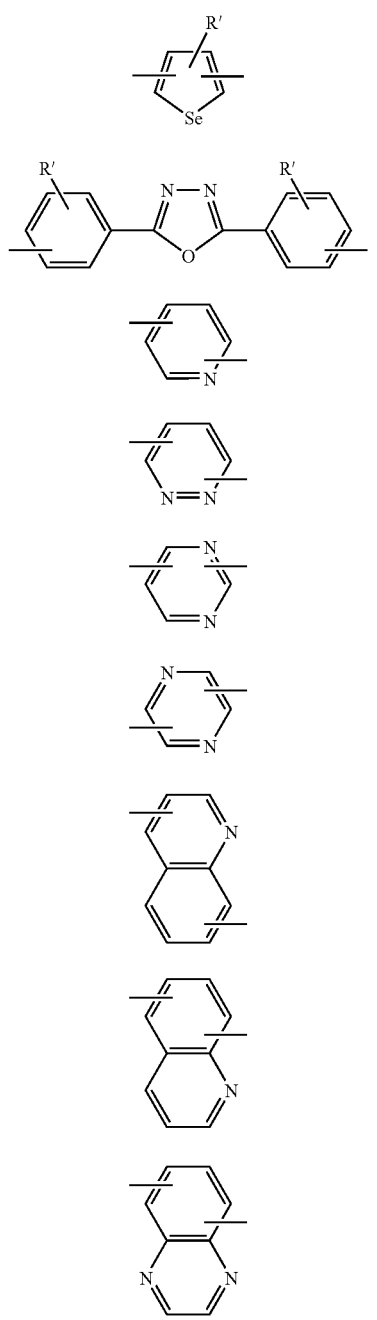

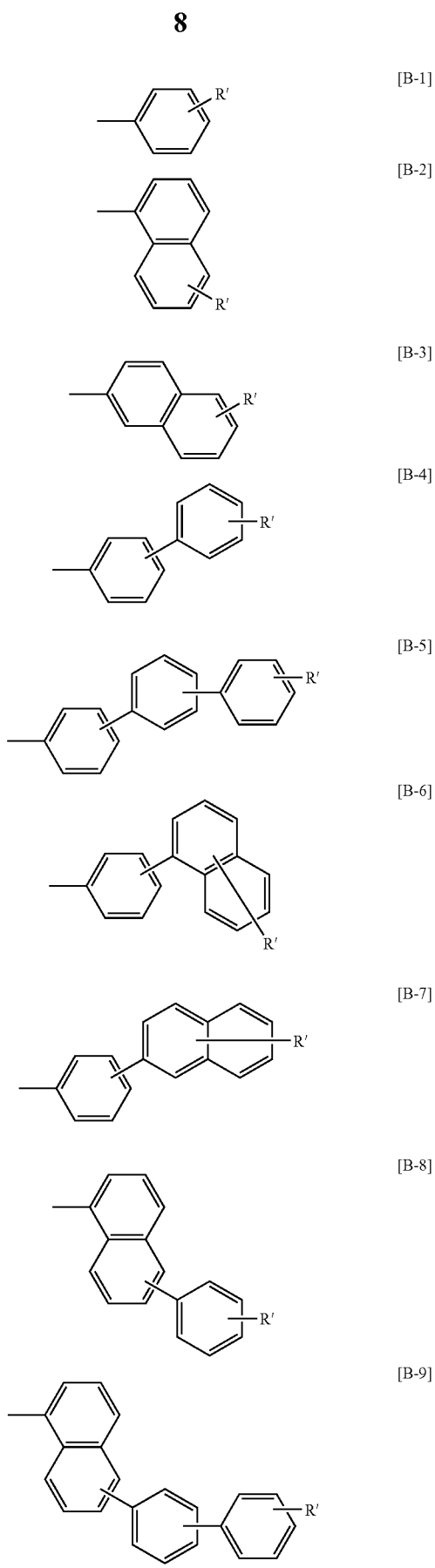

wherein R' is identical to or different from each other and one selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group.

In Formulae 3 to 6, $Ar_1$, $Ar_2$ and $Ar_3$ are identical to or different from each other, and each independently represented by any one of the formulae B1 through B-17 below:

-continued

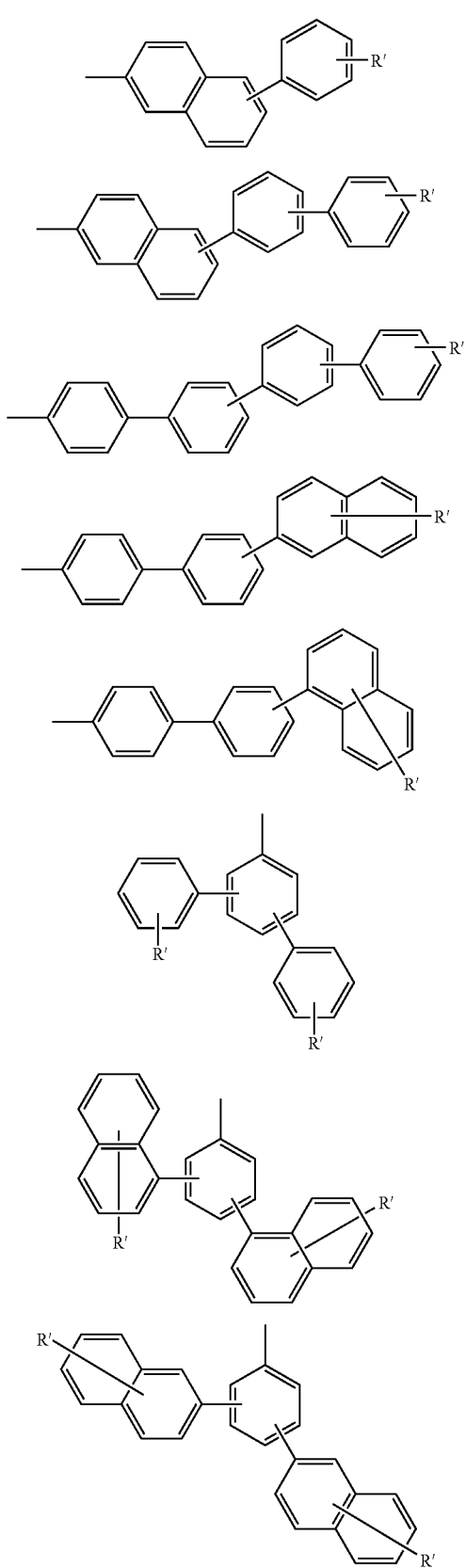

wherein R' is identical to or different from each other and one selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group.

The alkyl group used herein as a substituent may be a linear or branched alkyl group having 1 to 20 carbon atoms, preferably 1 to 12 carbon atoms, and more preferably 1 to 6 carbon atoms. Examples of the unsubstituted alkyl group are a methyl group, an ethyl group, an n-propyl group, an isopropyl group, a n-butyl group, an isobutyl group, a sec-butyl group, a t-butyl group, a pentyl group, an iso-amyl group and a hexyl group.

The cycloalkyl group used herein is a monovalent monocyclic system having 3 to 20 carbon atoms, preferably 3 to 10 carbon atoms, and more preferably 3 to 6 carbon atoms.

The heterocycloalkyl group used herein is a monovalent monocyclic system having 3 to 20 carbon atoms, preferably 3 to 10 carbon atoms, and more preferably 3 to 6 carbon atoms, 1, 2 or 3 carbon atoms of which are substituted with N, O, P and S.

The alkoxy group used herein as a substituent may be an oxygen-containing linear or branched alkoxy group having an alkyl moiety consisting of 1 to 20 carbon atoms, preferably 1 to 6 carbon atoms, and more preferably 1 to 3 carbon atoms. Examples of the alkoxy group are a methoxy group, an ethoxy group, a propoxy group, a butoxy group and a t-butoxy group. Such an alkoxy group can further be substituted by at least one halo atom such as fluoro, chloro and bromo to provide a haloalkoxy group. Examples of the haloalkoxy group are a fluoromethoxy group, a chloromethoxy group, a trifluoromethoxy group, a trifluoroethoxy group, a fluoroethoxy group and a fluoropropoxy group.

The aryl group as a substituent is used alone or in a combination, and is a carbocyclic aromatic system having 6 to 30 carbon atoms and one or more rings. The rings may be attached using a pendent manner or fused together. The term "aryl" includes aromatic radicals such as phenyl, naphthyl, tetrahydronaphthyl, indane and biphenyl. For example, the aryl group may be phenyl.

The aralkyl used herein is an alkyl group in which at leas one hydrogen atom is substituted with the aryl group.

The heteroaryl group used herein as a substituent is a monovalent monocyclic or bicyclic aromatic radical having at least one 5 to 30 membered ring(s) in which one, two or three atoms are N, O or S. The heteroaryl group may be a monovalent monocyclic or bicyclic aromatic radical in which the hetero atoms is oxidized or quaternized to form, for example, an N-oxide or a quaternary salt. Examples of the heteroaryl group are thienyl, benzothienyl, pyridyl, pyrazinyl, pyrimidinyl, pyridazinyl, quinolinyl, quinoxalinyl, imidazolyl, furanyl, benzofuranyl, thiazolyl, isoxazolyl, benzisoxazolyl, benzimidazolyl, triazolyl, pyrazolyl, pyrolyl, indolyl, 2-pyridonyl, N-alkyl-2-pyridonyl, pyrazinonyl, pyridazynonyl, pyrimidinonyl, oxazolonyl, corresponding N-oxides thereof (e.g., pyridyl N-oxide and quinolinyl N-oxide), and quaternary salts thereof, but are not limited thereto.

When the alkyl group, the alkoxy group, the aryl group, the heteroaryl group, the cycloalkyl group and the heterocycloalkyl group are substituted, the substituents may be at least one of —F; —Cl; —Br; —CN; —NO$_2$; —OH; a C1-C20alkyl group that is unsubstituted or substituted with —F, —Cl, —Br, —CN, —NO$_2$ or —OH; a C1-C20 alkoxy group that is unsubstituted or substituted with —F, —Cl, —Br, —CN, —NO$_2$ or —OH; a C6-C30 aryl group that is unsubstituted or substituted with a C1-C20 alkyl group, a C1-C20 alkoxy group, —F, —Cl, —Br, —CN, —NO$_2$ or —OH; a C2-C30 heteroaryl group that is unsubstituted or substituted with a C1-C20 alkyl group, a C1-C20 alkoxy group, —F, —Cl, —Br, —CN, —NO$_2$ or —OH; a C5-C20 cycloalkyl group that is unsubstituted or substituted with a C1-C20 alkyl group, a C1-C20 alkoxy group, —F, —Cl, —Br, —CN, —NO$_2$ or —OH; a C5-C30 heterocycloalkyl group that is unsubstituted or substituted with a C1-C20 alkyl group, a C1-C20 alkoxy group, —F, —Cl, —Br, —CN, —NO$_2$ or —OH; and —N(G6)(G7). Here, G6 and G7 are each independently a hydrogen atom; C1-C1 alkyl group; or a C6-C30 aryl group substituted with a C1-C10 alkyl group.

In particular, $R_1$ to $R_{17}$ are each independently selected from the group consisting of a hydrogen atom, a halogen atom, a cyano group, a hydroxyl group, a C1-C10 alkyl group, a C1-C10 alkoxy group and a substituted or unsubstituted derivative such as: a phenyl group, a biphenyl group, a pentalenyl group, an indenyl group, a naphthyl group, a biphenylenyl group, an anthracenyl group, an azulenyl group, a heptalenyl group, an acenaphthylenyl group, a phenalenyl group, a fluorenyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a fluorenyl group, a pyranthrenyl group, an ovalenyl group, a carbazolyl group, a thiophenyl group, an indolyl group, a purinyl group, a benzimidazolyl group, a quinolinyl group, a benzothiophenyl group, a parathiazinyl group, a pyrrolyl group, a pyrazolyl group, an imidazolyl group, an imidazolinyl group, an oxazolyl group, a thiazolyl group, a triazolyl group, a tetrazolyl group, an oxadiazolyl group, a pyridinyl group, a pyridazinyl group, a pyrimidinyl group, a pyrazinyl group, a thianthrenyl group, a cyclopentyl group, a cyclohexyl group, an oxiranyl group, a pyrrolidinyl group, a pyrazolidinyl group, an imidazolidinyl group, a piperidinyl group, a piperazinyl group, a morpholinyl group, a di(C6-C30 aryl)amino group, a tri(C6-C30 aryl) silyl group and derivatives thereof.

Here, the term "derivative" indicates the above-listed group in which at least one of the hydrogen atoms is substituted with the substituents described above.

The anthracene-based compound according to an embodiment of the present invention has high solubility in a solvent in the formation of an organic layer, high thermal stability since a glass transition temperature (Tg) is high due to a delocalized electron distribution and a rigid structure, and excellent electron injecting and transporting capability since the pyridinylquinoline-based compound or the pyridinylisoquinoline-based compound is introduced thereinto. Thus, an organic light emitting device employing the anthracene-based compound can have low driving voltage and high efficiency.

The compound according to an embodiment of the present invention may be represented by one of Formulae 7 to 50 below, but is not limited thereto.

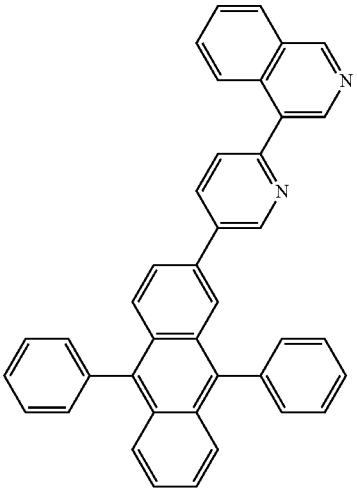

Formula 7

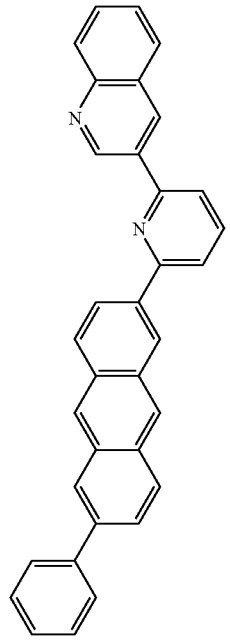

Formula 8

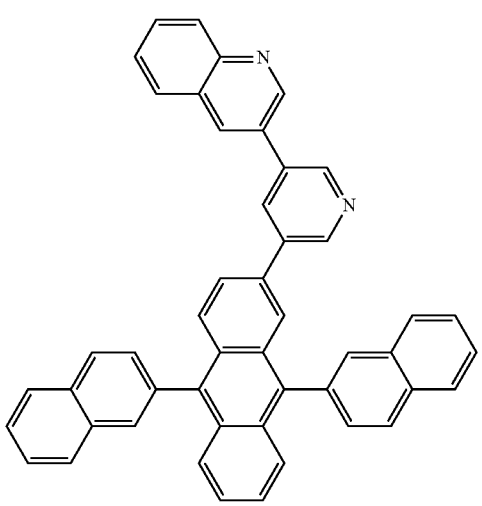

Formula 9

Formula 10
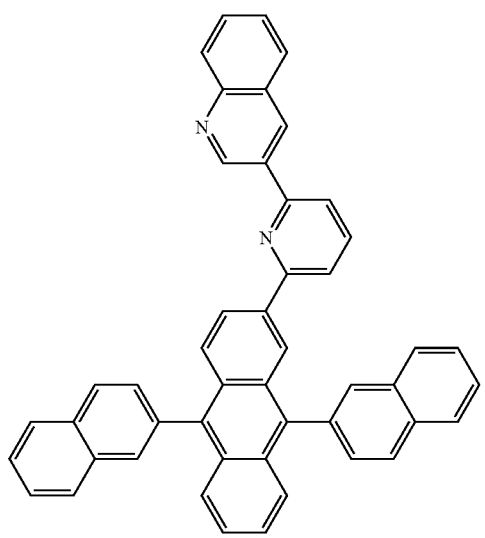
Formula 11
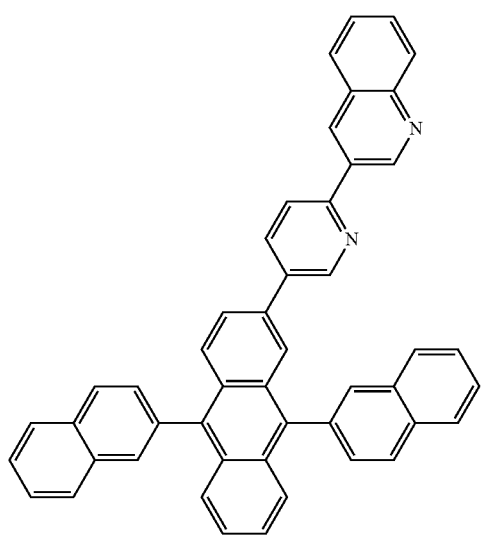
Formula 12
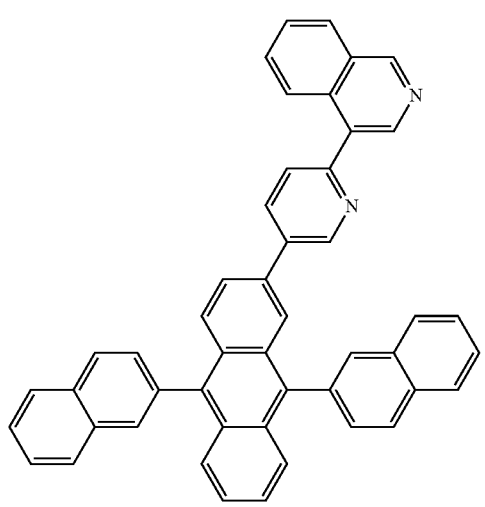
Formula 13
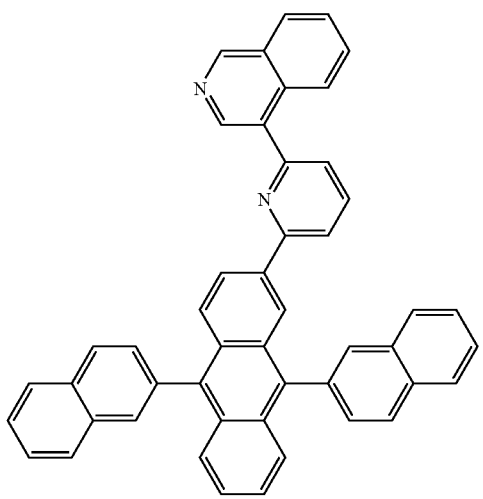
Formula 14
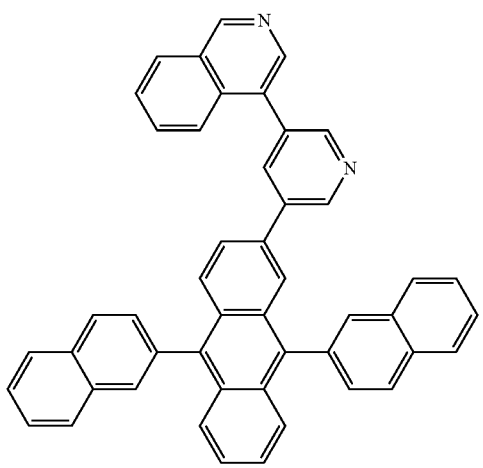
Formula 15
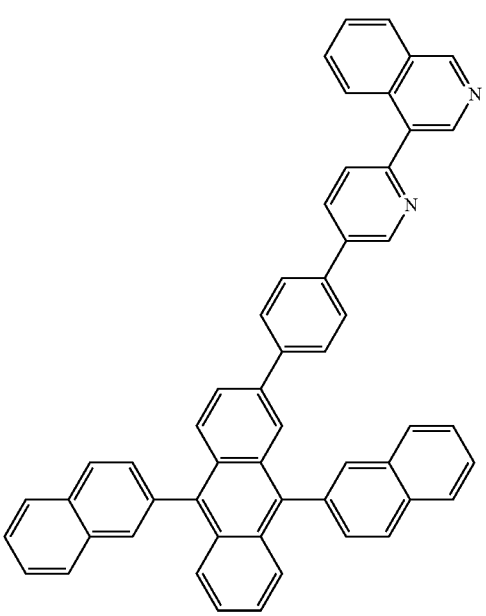

Formula 16
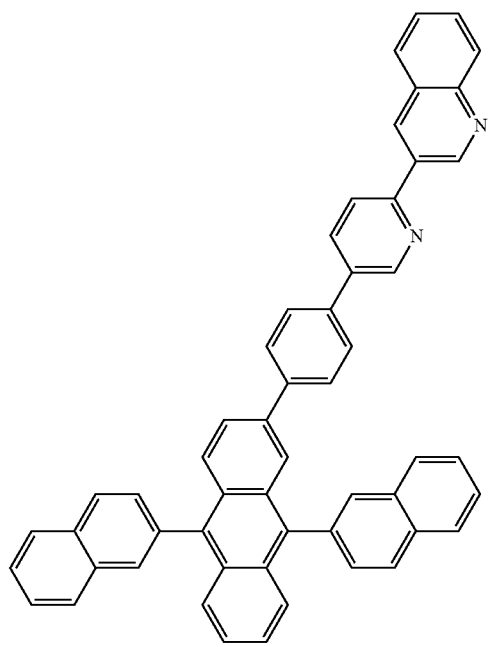
Formula 17
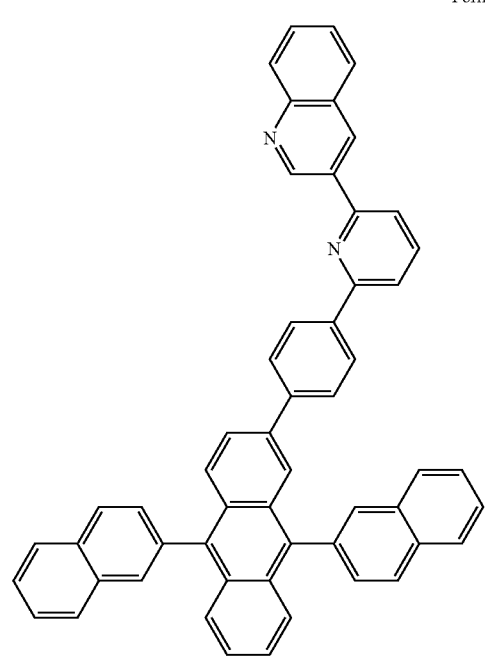
Formula 18
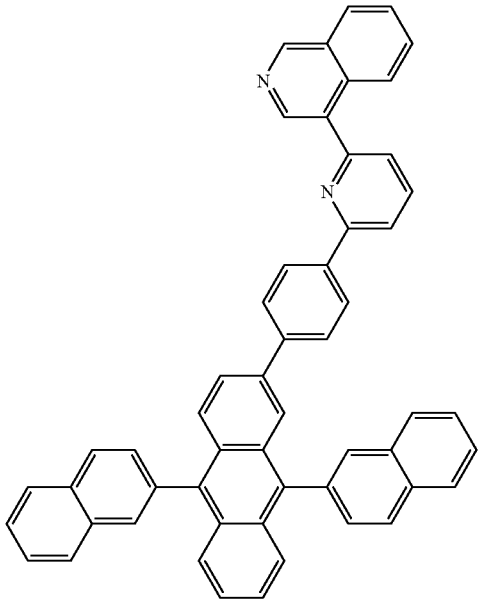
Formula 19
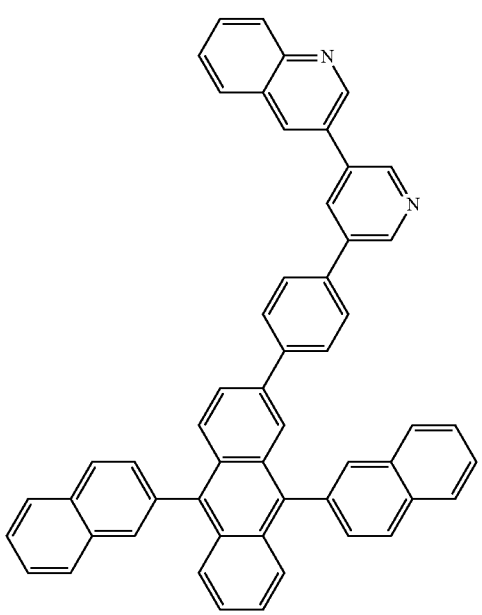

Formula 20
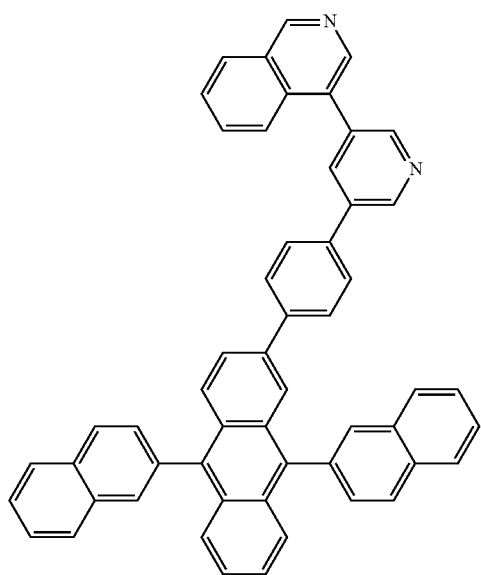
Formula 21
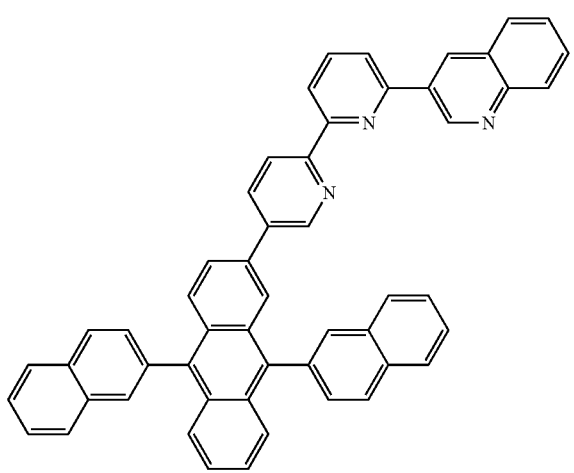
Formula 22
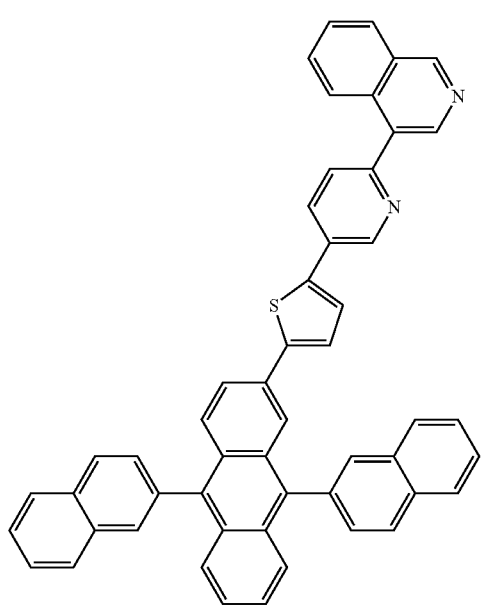
Formula 23
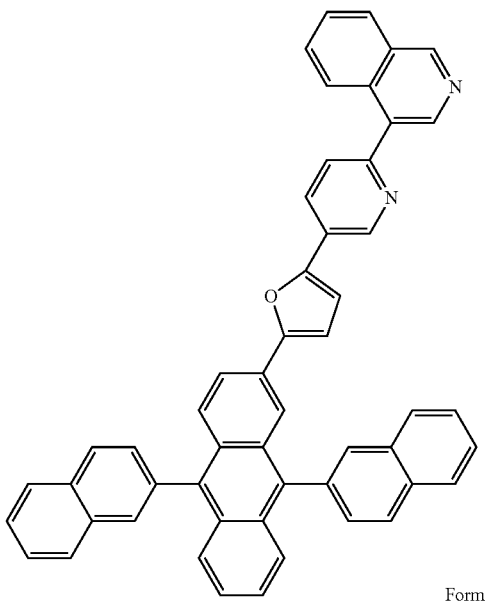
Formula 24
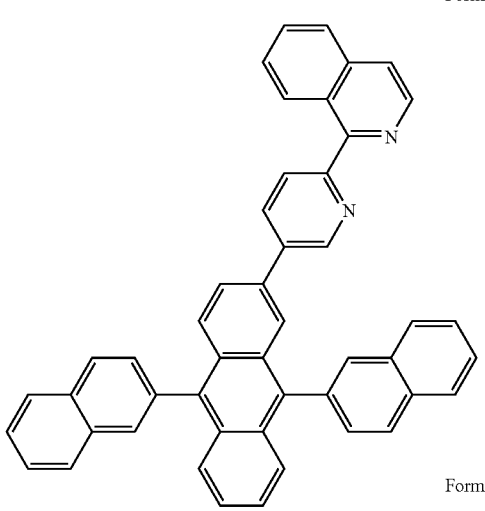
Formula 25
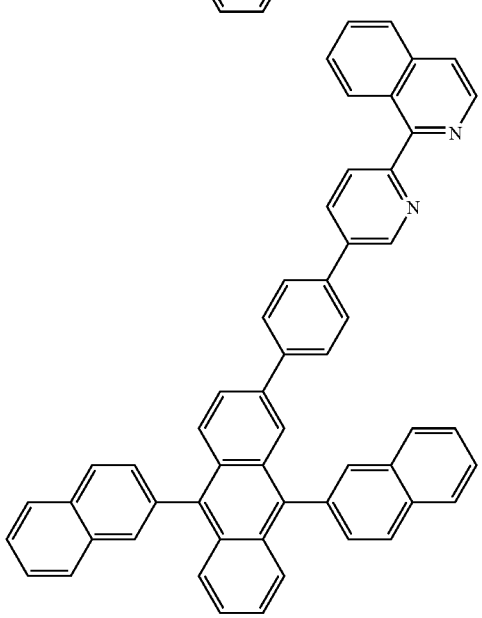

Formula 26
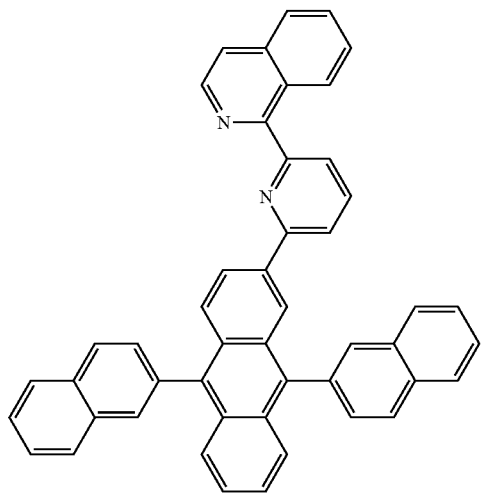
Formula 27
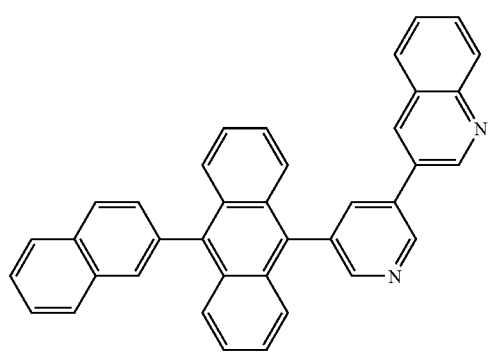
Formula 28
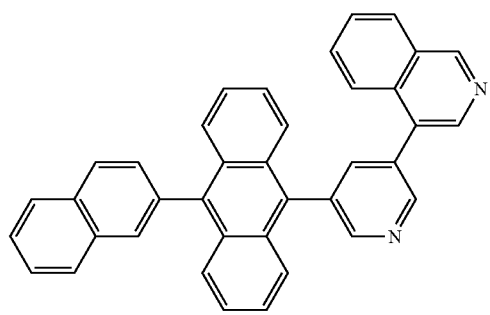
Formula 29
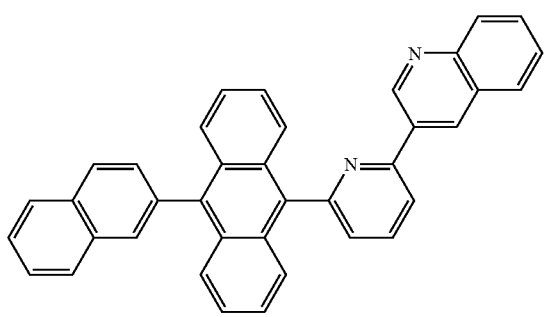
Formula 30
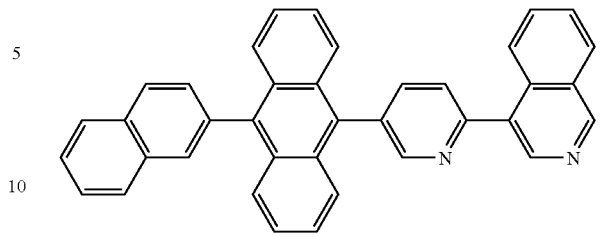
Formula 31
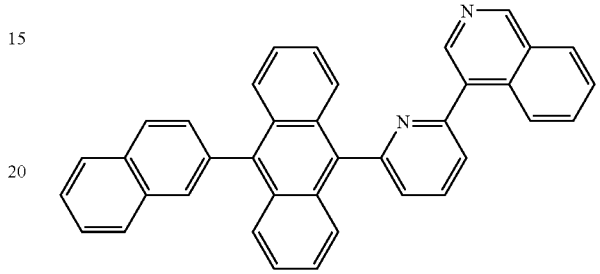
Formula 32
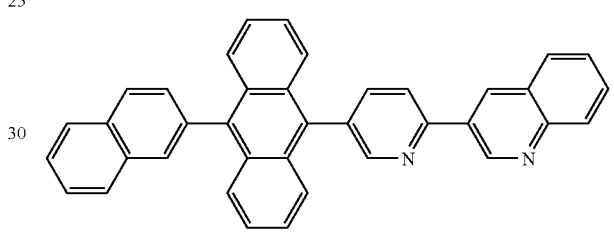
Formula 33
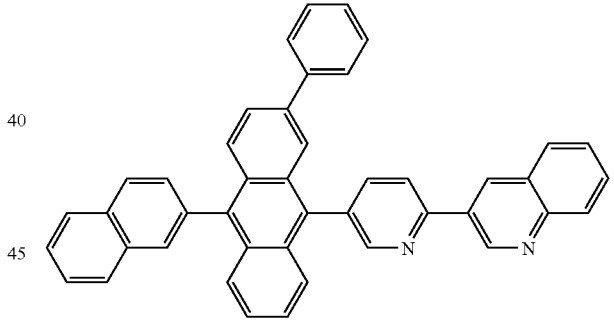
Formula 34
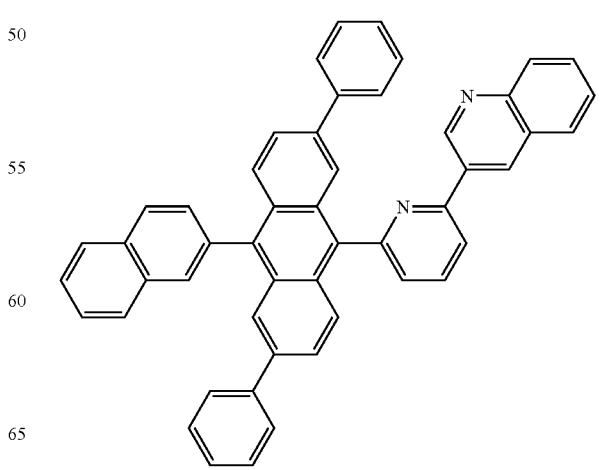

Formula 35
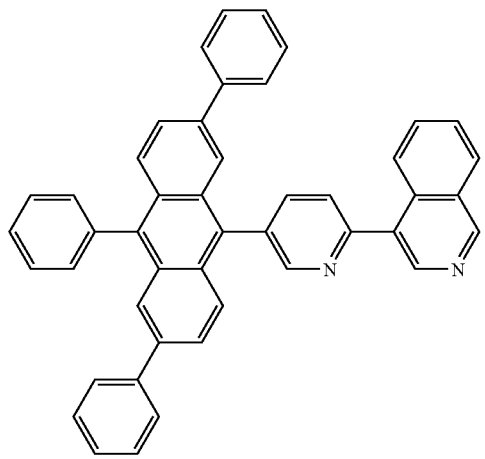
Formula 36
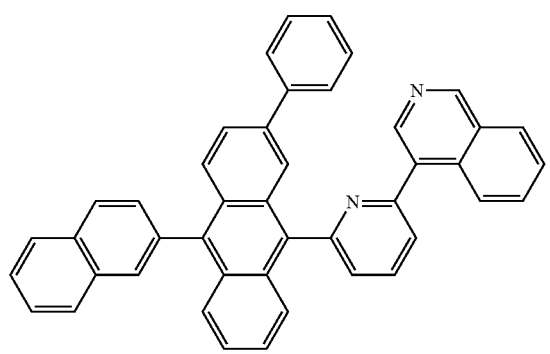
Formula 37
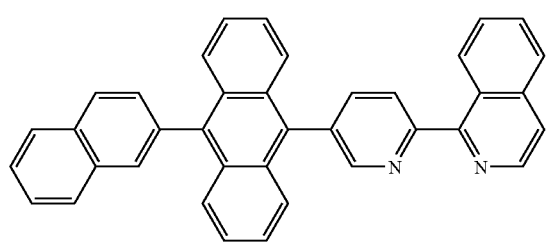
Formula 38
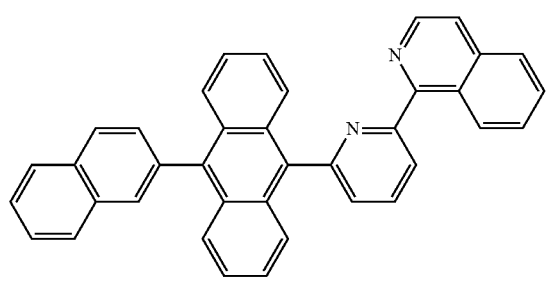
Formula 39
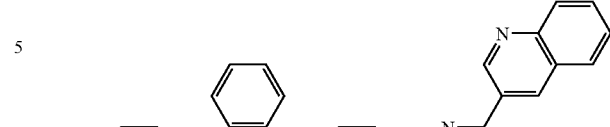
Formula 40
Formula 41
Formula 42
Formula 43
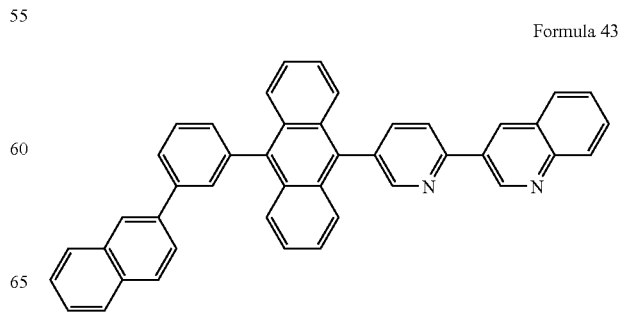

Formula 44

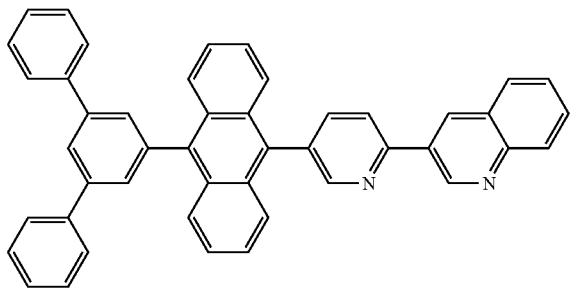

Formula 45

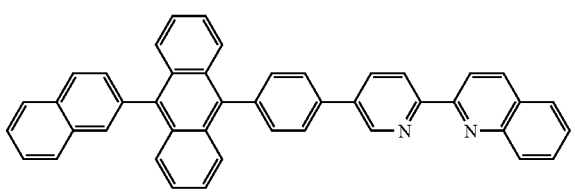

Formula 46

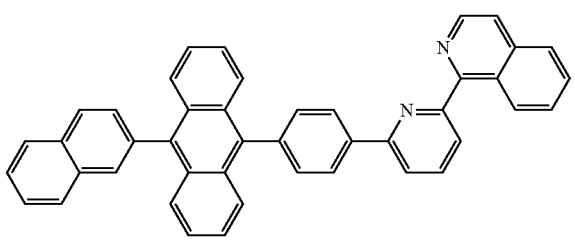

Formula 47

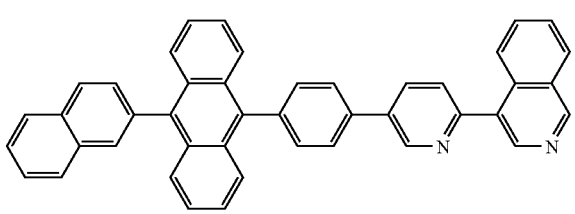

Formula 48

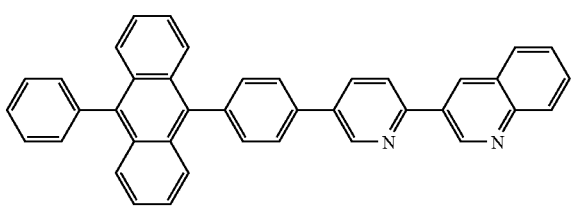

Formula 49

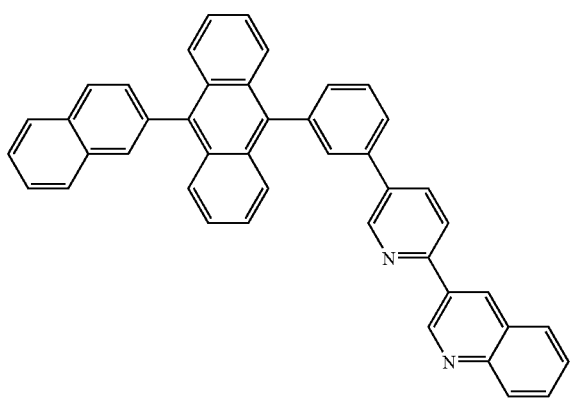

Formula 50

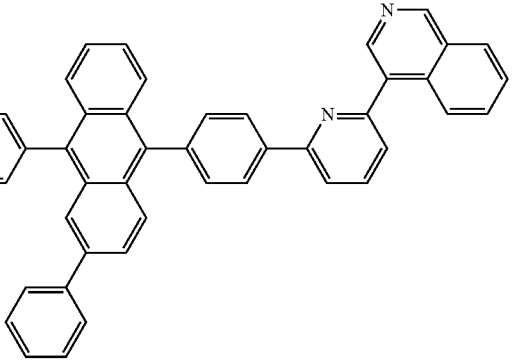

The compound according to an embodiment of the present invention may be synthesized using a synthesis principle that is commonly used in the art. A synthetic pathway of the compound is described with respect to synthesis examples.

An organic light emitting device according to an embodiment of the present invention may include a first electrode; a second electrode; and an organic layer interposed between the first electrode and the second electrode, wherein the organic layer includes at least one anthracene-based compound having a compound represented by Formula 1 or 2.

The anthracene-based compound is suitably used to form an organic layer, preferably an emitting layer, an electron injection layer, an electron transport layer or a hole blocking layer. An emitting layer of the organic light emitting device of an embodiment of the present invention may include a phosphorescent or fluorescent dopant for red, green, blue or white color. The phosphorescent dopant may be an organic metal compound including at least one element selected from the group consisting of Ir, Pt, Os, Ti, Zr, Hf, Eu, Tb and Tm.

The organic light emitting device of an embodiment of the present invention has improved emitting properties such as low driving voltage and high color purity by employing a compound having high solubility and thermal stability and capable of forming a stable organic layer when compared to a conventional organic light emitting device prepared using a solution coating method and having low stability of organic layer.

The organic light emitting device of an embodiment of the present invention may have various structures. That is, the organic light emitting device may further include at least one layer selected from the group consisting of a hole injection layer, a hole transport layer, a hole blocking layer, an electron blocking layer, an electron transport layer and an electron injection layer between the first electrode and the second electrode.

Figure 1B:
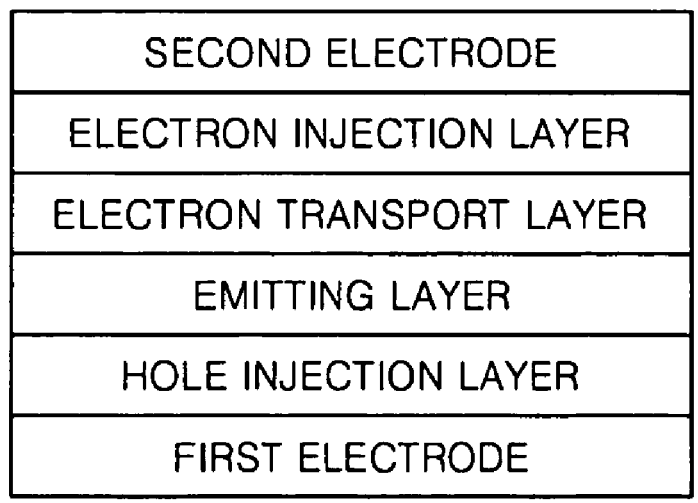
FIG. 1B is a schematic sectional view of an organic light emitting device according to another embodiment of the present invention.

More particularly, FIGS. 1A and 1B are schematic sectional views of organic light emitting devices according to embodiments of the present invention. The organic light emitting device of FIG. 1A has a structure of a first electrode/a hole injection layer/a hole transport layer/an emitting layer/an electron transport layer/an electron injection layer/a second electrode. The organic light emitting device of FIG. 1B has a structure of a first electrode/a hole injection layer/an emitting layer/an electron transport layer/an electron injection layer/a second electrode.

The organic layer in the organic light emitting device according to an embodiment of the present invention may further include an organic metal complex.

The organic metal complex is a compound having an organic ligand connected to a metal only by coordinate bonds.

Here, the metal may be an alkali metal (I) such as Li, Na, K, Rb and Cs; an alkaline earth metal (II) such as Mg, Ca, Sr and Ba; and a rare earth metal (III) such as Y, La, Ce, Pr, Nd, Sm, Eu, Er and Yb.

The ligands coordinated to the metal in the organic metal complex may be β-diketones such as acetyl acetone, 1,3-diphenyl-1,3-propanedioene, 2,2,6,6-tetramethyl-3,5-heptanedione, 1,1,1,2,2,3,3,-heptafluoro-7,7-dimethyl-4,6-octanedione and 1-phenyl-1,3-butanedione, salicyl aldehydes such as salicyl aldehyde and diethylaminosalicyl aldehyde, anthracene, naphthalene, phenanthrene, pyrene, tetracene, coronene, chrysene, fluorescein, perylene, phthaloperylene, naphthaloperylene, perinone, phthaloperinone, naphthaloperinone, diphenylbutadiene, tetraphenylbutadiene, coumarin, oxadiazole, aldazine, bisbenzoxazoline, bistyryl, pyrazine, cyclopentadiene, quinoline, aminoquinoline, benzoquinoline, or the like.

The amount of the organic metal complex may be in the range of 0.01 to 90 parts by weight, and preferably 0.1 to 60 parts by weight, based on 100 parts by weight of a solid that is used to form an organic layer. When the amount of the organic metal complex is less than 0.01 parts by weight, emitting efficiency is not sufficiently improved and electron injection effect is not sufficient. On the other hand, when the amount of the organic metal complex is more than 90 parts by weight, electron transporting capability may be decreased.

The organic layer in the organic light emitting device according to an embodiment of the present invention may further include an ionic salt such as an inorganic salt, an organic salt or a metal salt.

Examples of the ionic salt in the organic layer are: a Li-containing inorganic salt such as $LiClO_4$, $LiPF_6$, $LiBF_4$, $LiN(CF_3SO_2)_2$ and lithium trifluoromethane sulfonate; an organic salt such as tetraethylammonium tetrafluoroborate (TEA-$BF_4$), tetra-n-butylammonium tetrafluoroborate ($Bu_4N$—$BF_4$), tetraalkyl, aryl or heteroaryl quaternary ammonium salt such as tetra-n-alkylammonium toluenesulfonate, tetra-n-alkylammonium tetrafluoroborate, tetra-n-alkyl ammonium tetraphenylborate, tetra-n-alkyl ammonium toluenesulfonate, tetraalkylammonium tetrafluoro borate and tetra-n-alkyl ammonium tetraphenylborate; and a polymeric salt such as polystyrenesulfonate (PSS).

Examples of the metal salt have a metal such as Al (III), Mn (II), Zr (IV), Ti (II), Hf (IV), Ta (V), Nb (III) and V (II). The inorganic salt is prepared by substituting hydrogen atoms of an inorganic acid, and examples of the inorganic salt are a halide such as chloride, fluoride, bromide and iodide. The organic metal salt is prepared by substituting hydrogen atoms of an organic acid, an alcohol and a dialkylamide, and examples of the organic salt are: an organic acid salt such as carboxylic acid and phenol; and salts of alkoxides and dialkylamides.

Here, the carboxylic acid may be aliphatic or aromatic. The aliphatic carboxylic acid may have 1 to 24 carbon atoms, and may be a saturated or unsaturated aliphatic carboxylic acid. The aliphatic carboxylic acid may have one or more carboxyl groups or optionally a substituent such as an aryl group. Examples of the aliphatic carboxylic acid are a saturated aliphatic carboxylic acid such as acetic acid, propionic acid, octyl acid, iso-octyl acid, decanoic acid, lauric acid; an unsaturated aliphatic carboxylic acid such as oleic acid and ricinoleic acid; and a polyhydric (di or tri) carboxylic acid such as citric acid and oxalic acid. The aromatic carboxylic acid may have 7 to 24 carbon atoms and a substituent such as a C1-C8 alkyl group and a hydroxyl group. Examples of the aromatic carboxylic acid are benzoic acid, o-(t-butyl)benzoic acid, m-(t-butyl)benzoic acid, salicylic acid, m-(hydroxy)benzoic acid and p-(hydroxy)benzoic acid). The phenol may have 6 to 46 carbon atoms, a substituent such as a C1-C8 linear or branched alkyl group, a phenyl group and an aryl group, and a condensed ring, for example, an aromatic ring such as a benzene ring having a substituent ring. The phenol group may be a monovalent phenol or a polyvalent phenol. Examples of the phenol are phenol, naphthol, 4-phenylphenol and 2,2-bis (p-hydroxyphenyl)propane (bisphenol A). The alcohol forming alkoxide may have 1 to 10 carbon atoms, and examples are: a primary alcohol such as ethyl alcohol, n-propyl alcohol and n-butyl alcohol; a secondary alcohol such as isopropyl alcohol and s-butyl alcohol; a tertiary alcohol such as t-butyl alcohol; and a polyhydric alcohol such as ethylene glycol.

The dialkylamide salt may have a substituent and 2 to 24 carbon atoms. Examples of the dialkylamide salt are dimethylamide, diethylamide and N-methyl-N-ethylamide.

However, the listed salts are examples of ionic salts which can be used in the present invention, and any salts having cations and anions can be used herein.

The amount of the ionic salt may vary according to the use, element and thickness of an emitting layer. The amount of the ionic salt, however, may be in the range of 0.01 to 50 parts by weight, and preferably 1 to 30 parts by weight based on 100 parts by weight a solid that is used to form an organic layer. Here, when the amount of the ionic salt is less than 0.01 parts by weight, emitting efficiency of the organic light emitting device may not be sufficiently improved and break-down voltage may not be sufficiently reduced. On the other hand, when the amount of the ionic salt is more than 50 parts by weight, the organic light emitting device may not be properly operated due to excess concentration of ions.

Hereinafter, a method of preparing an organic light emitting device according to an embodiment of the present invention will be described with reference to FIG. 1A.

First, a first electrode is formed on a substrate, for example, by depositing or sputtering a high work-function material. The first electrode can be an anode. The substrate, which can be any substrate that is used in conventional organic light emitting devices, may be a glass substrate or a transparent plastic substrate with excellent mechanical strength, thermal stability, transparency, surface smoothness, ease of treatment, and waterproof. The material that is used to form the first electrode can be ITO, IZO, $SnO_2$, ZnO, or any transparent material which has high conductivity.

Then, a hole injection layer (HIL) can be formed on the first electrode by vacuum deposition, spin coating, casting, langmuir Blodgett (LB), or the like.

When the hole injection layer is formed by vacuum deposition, deposition conditions may vary according to a compound that is used to form the hole injection layer, and the structure and thermal properties of the hole injection layer to be formed. In general, however, conditions for vacuum deposition may include a deposition temperature of 100 to 500° C., a pressure of $10^{-8}$ torr to $10^{-3}$ torr, a deposition speed of 0.01 to 100 Å/sec, and a layer thickness of 10 Å to 5 μm.

When the hole injection layer is formed by spin coating, coating conditions may vary according to a compound that is used to form the hole injection layer, and the structure and thermal properties of the hole injection layer to be formed. In general, however, conditions for spin coating may include a coating speed of 2000 to 5000 rpm and a heat-treatment temperature of about 80 to 200° C. to remove a solvent after coating.

The thickness of the HIL may be in the range of about 100 to 10000 Å, and preferably in the range of 100 to 1000 Å. When the thickness of the HIL is less than 100 Å, the hole injecting ability of the HIL may be reduced. On the other hand, when the thickness of the HIL is greater than 10000 Å, a driving voltage of the device may be increased.

Then, a hole transport layer (HTL) can be formed on the HIL by vacuum deposition, spin coating, casting, LB, or the like. When the HTL is formed by vacuum deposition or spin coating, the conditions for deposition and coating are similar to those for the formation of the HIL, although conditions for the deposition and coating may vary according to the material that is used to form the HTL.

The thickness of the HTL may be in the range of about 50 to 1000 Å, and preferably 100 to 600 Å. When the thickness of the HTL is less than 50 Å, a hole transporting ability of the HTL may be reduced. On the other hand, when the thickness of the HTL is greater than 1000 Å, the driving voltage of the device may be increased.

Then, an emitting layer (EML) can be formed on the HTL by vacuum deposition, spin coating, casting, LB, or the like. When the EML is formed by vacuum deposition or spin coating, the conditions for deposition and coating are similar to those for the formation of the HIL, although the conditions for deposition and coating may vary according to the material that is used to form the EML.

The thickness of the EML may be in the range of about 100 to 1000 Å, and preferably in the range of 200 to 600 Å. When the thickness of the EML is less than 100 Å, the emitting ability of the EML may be reduced. On the other hand, when the thickness of the EML is greater than 1000 Å, the driving voltage of the device may be increased.

A hole blocking layer (HBL) can be formed on the HTL by vacuum deposition, spin coating, casting, LB, or the like, to prevent diffusion of triplet excitons or holes into an electron transport layer when the phosphorescent dopant is used to form the EML. When the HBL is formed by vacuum deposition or spin coating, the conditions for deposition and coating are similar to those for the formation of the HIL, although the conditions for deposition and coating may vary according to the material that is used to form the HBL. The HBL may be formed of a compound represented by one of Formulae 3 to 6, an oxadiazole derivative, a triazole derivative, a phenanthroline derivative, BCP or an aluminum complex.

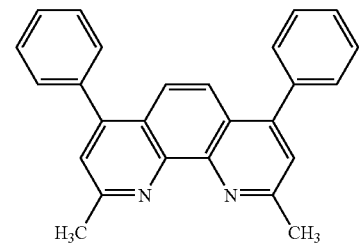

phenanthroline-containing organic compound

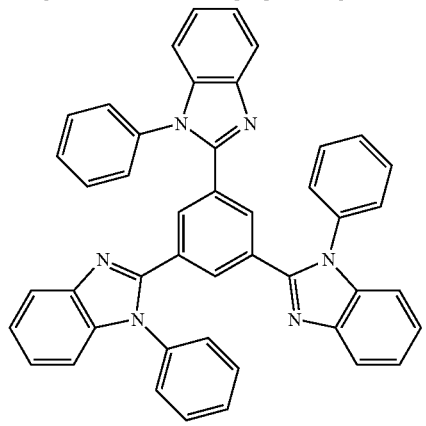

imidazole-containing organic compound

-continued

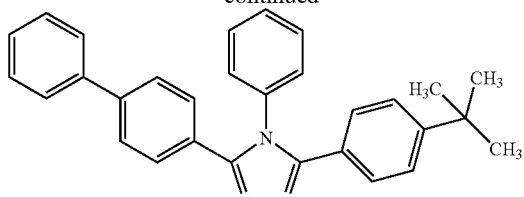

triazole-containing organic compound

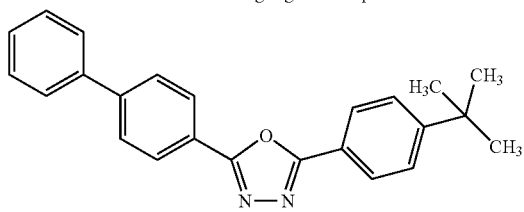

oxadiazole-containing compound

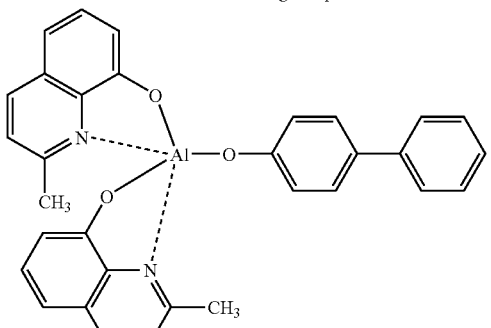

BAlq

The thickness of the HBL may be in the range of about 50 to 1000 Å, and preferably in the range of 100 to 300 Å. When the thickness of the HBL is less than 50 Å, the hole blocking ability of the HBL may be reduced. On the other hand, when the thickness of the HBL is greater than 1000 Å, the driving voltage of the device may be increased.

Then, an electron transport layer (ETL) is formed by vacuum deposition, spin coating, casting, or the like. When the ETL is formed by vacuum deposition or spin coating, the conditions for deposition and coating are, in general, similar to those for the formation of the HIL, although the conditions for the deposition and coating conditions may vary according to the material that is used to form the ETL. The ETL may be formed of a known material in the art which stably transports injected electrons from a cathode, for example, a compound represented by one of Formulae 3 to 6, an oxazole-based compound, an iso-oxazole-based compound, a triazole-based compound, an isothiazole-based compound, an oxadiazole-based compound, a thiadiazole-based compound, a perylene-based compound, an aluminum complex such as tris(8-quinolinolato)-aluminium (Alq3), BAlq, SAlq, Almq3, a gallium complex such as Gaq'2OPiv, Gaq'2OAc and 2(Gaq'2), or the like.

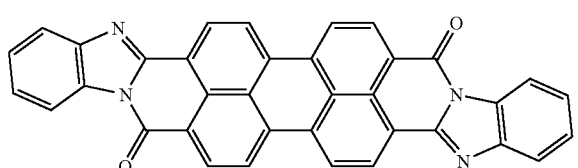

perylene-based compound

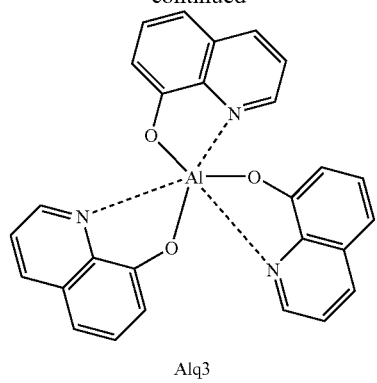

Alq3

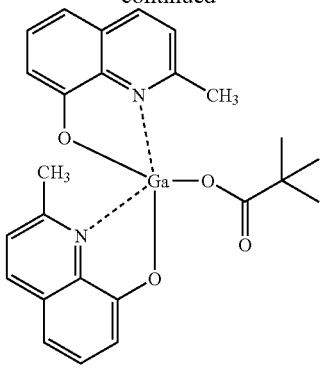

Gaq'2OPiv

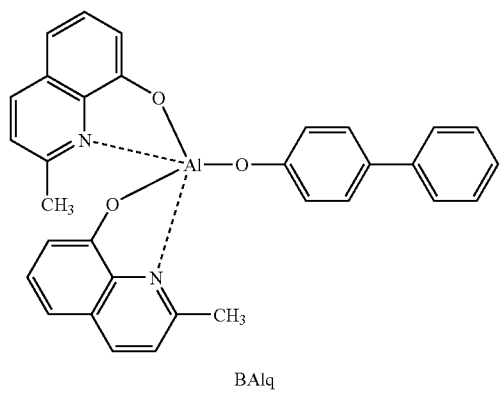

BAlq

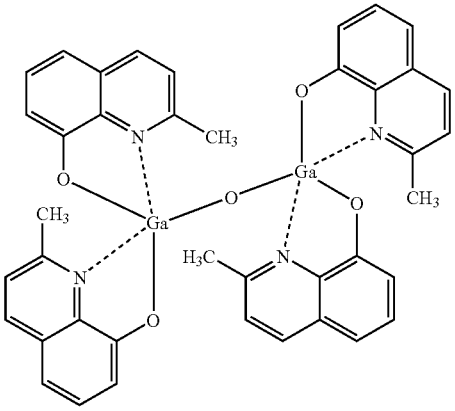

Gaq'2Oac

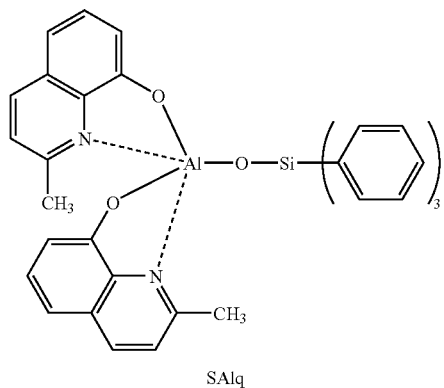

SAlq

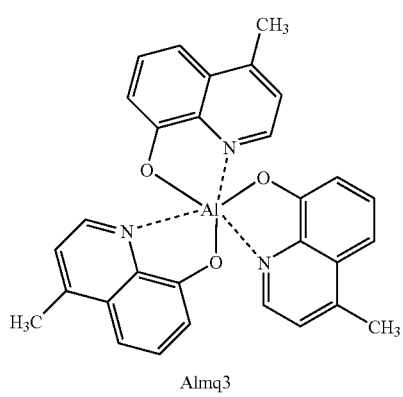

Almq3

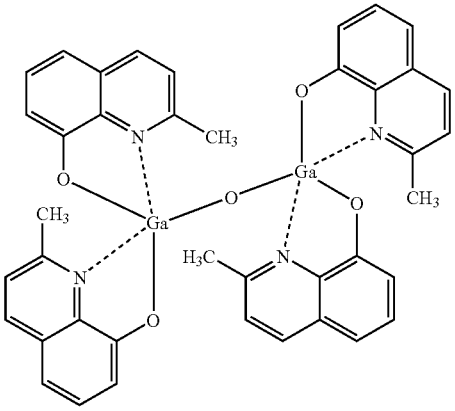

2(Gaq'2)

The thickness of the ETL may be in the range of about 100 to 1000 Å, and preferably 200 to 500 Å. When the thickness of the ETL is less than 100 Å, the electron transporting ability of the ETL may be reduced. On the other hand, when the thickness of the ETL is greater than 1000 Å, the driving voltage of the device may be increased.

Then, an electron injection layer (EIL), which is formed of a material allowing easy injection of electrons from a cathode, can be formed on the ETL. The material that is used to form the EIL is not limited.

The EIL may be formed of LiF, NaCl, CsF, $Li_2O$, BaO, or the like, which is known in the art. Conditions for the deposition of the EIL are, in general, similar to conditions for the formation of the HIL, although they may vary according to the material that is used to form the EIL.

The thickness of the EIL may be in the range of about 1 to 100 Å, and preferably 5 to 50 Å. When the thickness of the EIL is less than 1 Å, the electron injecting ability of the EIL may be reduced. On the other hand, when the thickness of the EIL is greater than 100 Å, the driving voltage of the device may be increased.

Finally, a second electrode can be formed on the EIL by vacuum deposition, sputtering, or the like. The second electrode can be used as a cathode. The second electrode may be formed of a low work-function metal, alloy, electrically conductive compound or a combination of these. In detail, the second electrode may be formed of Li, Mg, Al, Al—Li, Ca, Mg—In, Mg—Ag, or the like. Alternatively, a transparent cathode formed of ITO or IZO can be used to produce a top emission light emitting device.

Hereinafter, the present invention will be described in greater detail with reference to the following examples. The following examples are for illustrative purposes only and are not intended to limit the scope of the invention.

EXAMPLE 1

1) Synthesis of 3-(5-bromo-pyridin-3-yl)-quinoline 1.11 g (4.7 mmol) of 3,5-dibromo-pyridin, 1.0 g (3.92 mmol) of 3-(4,4,5,5-tetramethyl-[1,3,2]dioxaborolan-2-yl)-quinoline, 0.45 g of tetrakis(triphenylphosphine)palladium (0), 7.84 ml of 2 M $K_2CO_3$ and 1.26 g of tetrabutylammoniumbromide were added to a 100 ml round-bottom flask in an argon atmosphere, and 30 ml of THF and 15 ml of toluene were added thereto. Then, the mixture was refluxed at 100° C. for 16 hours. When the mixture solution turned dark brown, water was added thereto and the mixture was subject to extraction using chloroform. Then, an organic layer extracted therefrom was dried using anhydrous magnesium sulfate and filtered. A solvent was removed and the resultant was separated using a silica gel column chromatography to obtain 1.1 g of white solid 3-(5-bromo-pyridin-3-yl)-quinoline which was identified by an atmospheric pressure chemical ionization (APCI) using LCMS (SHIMADZU, LCMS-IT-TOF). As a result, a main peak was observed at [M+H]+=285.

2) Synthesis of a Compound Represented by Formula 9

0.61 g (2.15 mmol) of 3-(5-bromo-pyridin-3-yl)-quinoline, 1.0 g (1.8 mmol) of 2-(9,10-di-naphthalene-2-yl-anthracen-2-yl)-4,4,5,5-tetramethyl-[1,3,2]dioxaborolane, 3.6 ml of 1 M $K_3PO_4$ and 20 ml of dioxane were added to a 100 ml round-bottom flask in an argon atmosphere, and the mixture was refluxed at 120° C. for 36 hours. When the reaction is completed, the reaction solution was cooled to room temperature, and 100 ml of toluene and 100 ml of distilled water were added thereto to extract an organic layer. The collected organic layer was dried using $MgSO_4$ and concentrated. The resultant was separated using a silica gel chromatography. Here, an elute solution obtained therefrom was concentrated and dried to obtain 1.1 g of a solid compound represented by Formula 9 which was identified by APCI using LCMS. As a result, a main peak was observed at [M+H]+=635.

EXAMPLE 2

1) Synthesis of 3-(6-bromo-pyridin-3-yl)-quinoline 1.11 g (4.7 mmol) of 2,6-dibromo-pyridin, 1.0 g (3.92 mmol) of 3-(4,4,5,5-tetramethyll-[1,3,2]dioxaborolan-2-yl)-quinoline, 0.45 g of tetrakis(triphenylphosphine)palladium (0), 7.84 ml of 2M $K_2CO_3$ and 1.26 g of tetrabutylammoniumbromide were added to a 100 ml round-bottom flask in an argon atmosphere, and 30 ml of THF and 15 ml of toluene were added thereto. Then, the mixture was refluxed at 100° C. for 16 hours. When the mixture solution turned dark brown, water was added thereto and the mixture was subject to extraction using chloroform. Then, an organic layer extracted therefrom was dried using anhydrous magnesium sulfate and filtered. A solvent was removed and the resultant was separated using a silica gel column chromatography to obtain 0.8 g of white solid 3-(6-bromo-pyridin-2-yl)-quinoline which was identified by APCI using LCMS. As a result, a main peak was observed at [M+H]+=285.

2) Synthesis of a Compound Represented by Formula 10

0.6 g (2.15 mmol) of 3-(6-bromo-pyridin-2-yl)-quinoline, 1.0 g (1.8 mmol) of 2-(9,10-di-naphthalene-2-yl-anthracene-2-yl)-4,4,5,5-tetramethyl-[1,3,2]dioxaborolan, 3.6 ml of 1 M $K_3PO_4$ and 20 ml of dioxane were added to a 100 ml round-bottom flask in an argon atmosphere, and the mixture was refluxed at 120° C. for 36 hours. When the reaction is completed, the reaction solution was cooled to room temperature, and 100 ml of toluene and 100 ml of distilled water were added thereto to extract an organic layer. The collected organic layer was dried using $MgSO_4$ and concentrated. The resultant was separated using a silica gel chromatography. An elute solution obtained therefrom was concentrated and dried to obtain 0.9 g of a compound represented by Formula 10 which was identified by APCI using LCMS. As a result, a main peak was observed at [M+H]+=635.

EXAMPLE 3

1) Synthesis of 3-(5-bromo-pyridin-2-yl)-quinoline 1.1 g (4.7 mmol) of 2,5-dibromo-pyridin, 1.0 g (3.92 mmol) of 3-(4,4,5,5-tetramethyl-[1,3,2]dioxaborolan-2-yl)-quinoline, 0.45 g of tetrakis(triphenylphosphine)palladium (0), 7.84 ml of 2M $K_2CO_3$ and 1.26 g of tetrabutylammoniumbromide were added to a 100 ml round-bottom flask in an argon atmosphere, and 30 ml of THF and 15 ml of toluene were added thereto. Then, the mixture was refluxed at 100° C. for 16 hours. When the mixture solution turned dark brown, water was added thereto and the mixture was subject to extraction using chloroform. Then, an organic layer extracted therefrom was dried using anhydrous magnesium sulfate and filtered. A solvent was removed and the resultant was separated using a silica gel column chromatography to obtain 1.2 g of white solid 3-(5-bromo-pyridin-2-yl)-quinoline which was identified by APCI using LCMS. As a result, a main peak was observed at [M+H]+=285.

2) Synthesis of a Compound Represented by Formula 11

0.62 g (2.15 mmol) of 3-(5-bromo-pyridin-2-yl)-quinoline, 1.0 g (1.8 mmol) of 2-(9,10-di-naphthalene-2-yl-anthracene-2-yl)-4,4,5,5-tetramethyl-[1,3,2]dioxaborolan, 3.6 ml of 1 M $K_3PO_4$ and 20 ml of dioxane were added to a 100 ml round-bottom flask in an argon atmosphere, and the mixture was refluxed at 120° C. for 36 hours. When the reaction is completed, the reaction solution was cooled to room temperature, and 100 ml of toluene and 100 ml of distilled water were added thereto to extract an organic layer. The collected organic layer was dried using $MgSO_4$ and concentrated. The resultant was separated using a silica gel chromatography. An elute solution obtained therefrom was concentrated and dried to obtain 1.1 g of a compound represented by Formula 11 which was identified by APCI using LCMS. As a result, a main peak was observed at [M+H]+=635.

Figure 2A:
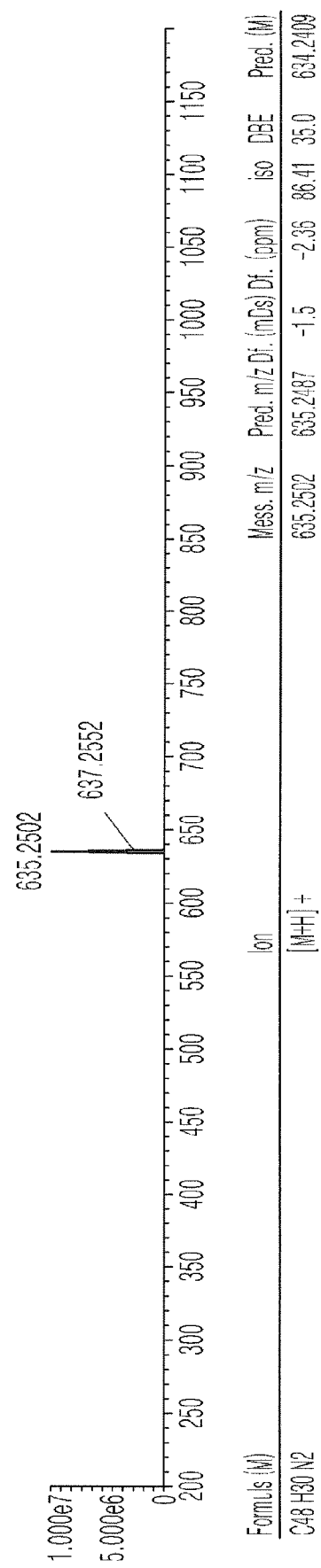
FIG. 2A is a graph illustrating liquid chromatography-mass spectrometry (LCMS) results of a compound prepared according to Example 3.
Figure 2B:
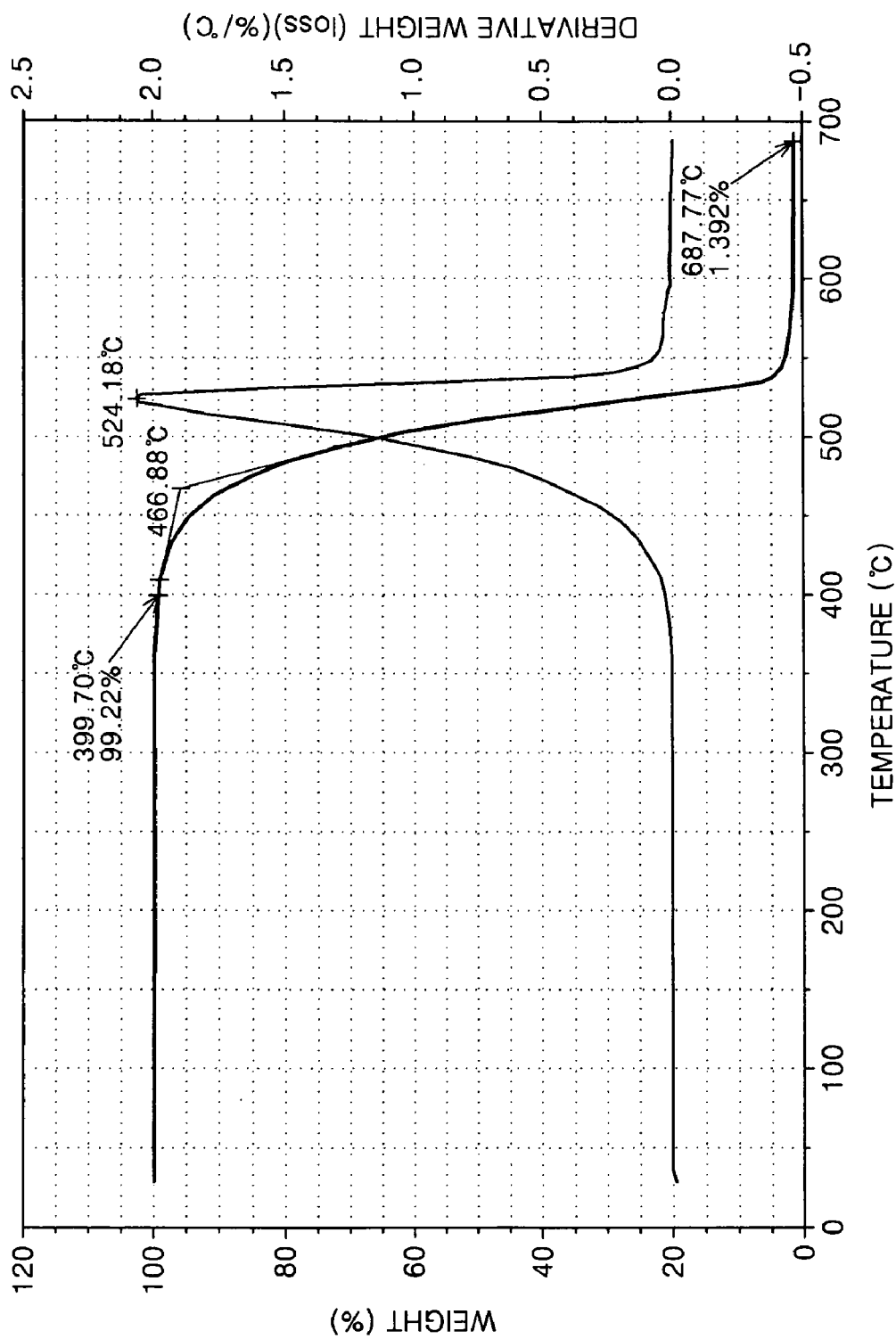
FIG. 2B is a graph illustrating thermogravimetric analysis (TGA) results of a compound prepared according to Example 3.
Figure 2C:
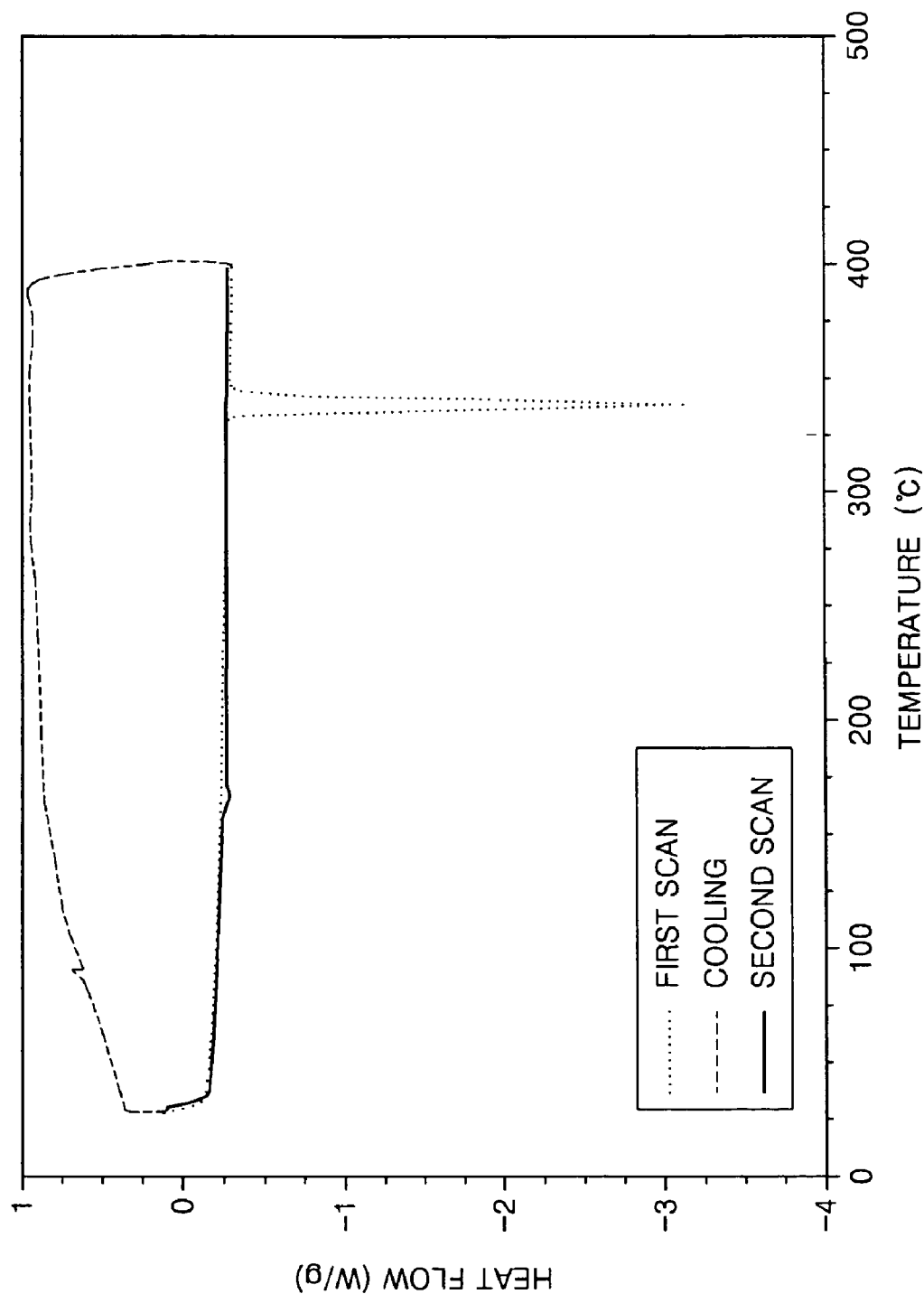
FIG. 2C is a graph illustrating differential scanning calorimetry (DSC) of a compound prepared according to Example 3.

FIG. 2A is a graph illustrating LCMS results of a compound prepared according to Example 3. In addition, thermal analysis of the compound of Formula 11 was performed using a thermo gravimetric analysis (TGA) in a $N_2$ atmosphere at a temperature in the range of room temperature to 600° C. at 10° C./min in a Pt pan in a disposable Al pan and a differential scanning calorimetry (DSC) at a temperature in the range of room temperature to 400° C. in a disposable Al pan. As a result, Td was 467° C. and Tg was 163° C. FIG. 2B is a graph illustrating thermogravimetric analysis (TGA) results of the compound of Formula 11 prepared according to Example 3 and FIG. 2C is a graph illustrating differential scanning calorimetry (DSC) of the compound of Formula 11 prepared according to Example 3.

EXAMPLE 4

1) Synthesis of 4-(5-bromo-pyridin-2-yl)-isoquinoline 4-(5-bromo-pyridin-2-yl)-isoquinoline was synthesized in the same manner as in Example 1-1), except that 2,5-dibromo-pyridin was used instead of 3,5-dibromo-pyridin and 4-(4,4,5,5-tetramethyl-[1,3,2]dioxaborolan-2-yl)-isoquinoline was used instead of 3-(4,4,5,5-tetramethyl-[1,3,2]dioxaborolan-2-yl)-quinoline. The 4-(5-bromo-pyridin-2-yl)-isoquinoline was identified by APCI using LCMS. As a result, a main peak was observed at [M+H]+=285.

2) Synthesis of a Compound Represented by Formula 12

A compound represented by Formula 12 was synthesized in the same manner as in Example 1-2), except that 4-(5-bromo-pyridin-2-yl)-isoquinoline was used instead of 3-(5-bromo-pyridin-3-yl)-quinoline. The compound of Formula 12 was identified by APCI using LCMS. As a result, a main peak was observed at [M+H]+=635.

EXAMPLE 5

1) Synthesis of 4-(6-bromo-pyridin-2-yl)-isoquinoline 4-(6-bromo-pyridin-2-yl)-isoquinoline was synthesized in the same manner as in Example 1-1), except that 2,6-dibromo-pyridin was used instead of 3,5-dibromo-pyridin and 4-(4,4,5,5-tetramethyl-[1,3,2]dioxaborolan-2-yl)-isoquinoline was used instead of 3-(4,4,5,5-tetramethyl-[1,3,2]dioxaborolan-2-yl)-quinoline. The 4-(6-bromo-pyridin-2-yl)-isoquinoline was identified by APCI using LCMS. As a result, a main peak was observed at [M+H]+=285.

2) Synthesis of a Compound Represented by Formula 13

A compound represented by Formula 13 was synthesized in the same manner as in Example 1-2), except that 4-(6-bromo-pyridin-2-yl)-isoquinoline was used instead of 3-(5-bromo-pyridin-3-yl)-quinoline. The compound of Formula 13 was identified by APCI using LCMS. As a result, a main peak was observed at [M+H]+=635.

EXAMPLE 6

1) Synthesis of 3-[5-(4-bromo-phenyl)-pyridin-2-yl]-quinoline 1.0 g (3.51 mmol) of 3-[5-(4-bromo-phenyl)-pyridin-2-yl]-quinoline, 2.8 g (14 mmol) of 4-bromophenylboric acid, 0.4 g of tetrakis(triphenylphosphine)palladium(0), 7 ml of 2 M $K_2CO_3$ and 1.2 g of tetrabutylammoniumbromide were added to a 100 ml round-bottom flask in an argon atmosphere, and 30 ml of THF and 15 ml of toluene were added thereto. Then, the mixture was refluxed at 100° C. for 12 hours. When the reaction is completed, water was added thereto and the mixture was subject to extraction using chloroform. Then, an organic layer extracted therefrom was dried using anhydrous magnesium sulfate and filtered. A solvent was removed and the resultant was separated using a silica gel column chromatography to obtain 0.54 g of white solid 3-[5-(4-bromo-phenyl)-pyridin-2-yl]-quinoline.

2) Synthesis of a Compound Represented by Formula 16

0.5 g (1.38 mmol) of 3-[5-(4-bromo-phenyl)-pyridin-2-yl]-quinoline, 1.0 g (1.8 mmol) of 2-(9,10-di-naphthalene-2-yl-anthracene-2-yl)-4,4,5,5-tetramethyl-[1,3,2]dioxaborolan, 3.6 ml of 1M $K_3PO_4$ and 20 ml of dioxane were added to a 100 ml round-bottom flask in an argon atmosphere, and the mixture was refluxed at 120° C. for 36 hours. When the reaction is completed, the reaction solution was cooled to room temperature, and 100 ml of toluene and 100 ml of distilled water were added thereto to extract an organic layer. The collected organic layer was dried using $MgSO_4$ and concentrated. The resultant was separated using a silica gel chromatography. An elute solution obtained therefrom was concentrated and dried to obtain 0.67 g of a compound represented by Formula 16 which was identified by APCI using LCMS. As a result, a main peak was observed at [M+H]+=710.

EXAMPLE 7

Synthesis of a Compound Represented by Formula 30

A compound represented by Formula 30 was synthesized in the same manner as in Example 4-2), except that 4,4,5,5-tetramethyl-2-(10-naphthalene-2-yl-anthracene-9-yl)-[1,3,2]dioxaborolan was used instead of 2-(9,10-di-naphthalene-2-yl-anthracene-2-yl)-4,4,5,5-tetramethyl-[1,3,2]dioxaborolan.

EXAMPLE 8

Synthesis of a Compound Represented by Formula 32

A compound represented by Formula 32 was synthesized in the same manner as in Example 3-2), except that 4,4,5,5-tetramethyl-2-(10-naphthalene-2-yl-anthracene-9-yl)-[1,3,2]dioxaborolan was used instead of 2-(9,10-di-naphthalene-2-yl-anthracene-2-yl)-4,4,5,5-tetramethyl-[1,3,2]dioxaborolan. The compound of Formula 32 was identified by APCI using LCMS. As a result, a main peak was observed at [M+H]+=509.

EXAMPLE 9

Synthesis of a Compound Represented by Formula 42

A compound represented by Formula 42 was synthesized in the same manner as in Example 6-2), except that 4,4,5,5-tetramethyl-2-(10-naphthalene-2-yl-anthracene-9-yl)-[1,3,2]dioxaborolan was used instead of 2-(9,10-di-naphthalene-2-yl-anthracene-2-yl)-4,4,5,5-tetramethyl-[1,3,2]dioxaborolan. The compound of Formula 42 was identified by APCI using LCMS. As a result, a main 11 peak was observed at [M+H]+=585.

EXAMPLE 10

Manufacturing and Evaluating Organic Light Emitting Devices

An organic light emitting device having the following structure was manufactured using a compound represented by Formula 9 of Example 1 as an electron transport layer, a compound represented by Formula 51 as a hole injection layer, a compound represented by Formula 52 as a hole transport layer, a compound represented by Formula 53 as a host of an emitting layer and a compound represented by Formula 54 as a dopant of the emitting layer: ITO/compound of Formula 51(600 Å)/compound of Formula 52(300 Å)/compound of Formula 53:compound of Formula 54(300 Å)/compound of Formula 9(250 Å)/LiF(6 Å)/Al(1500 Å).

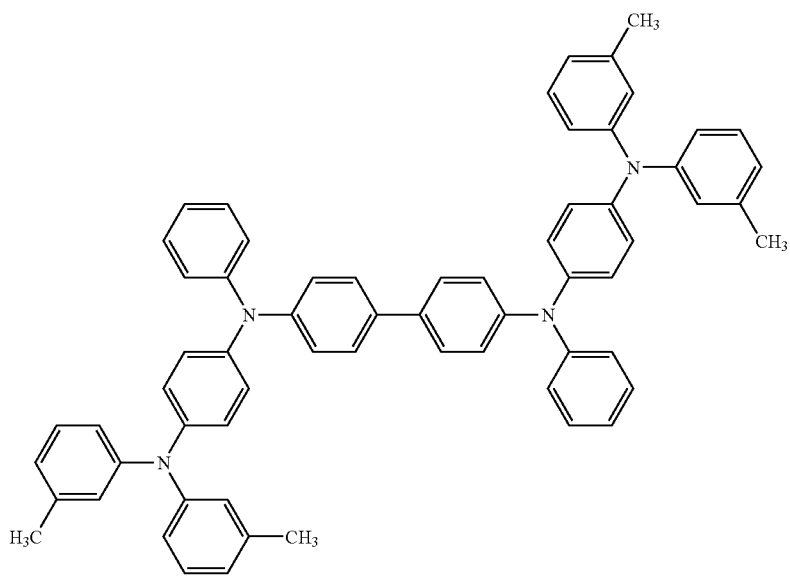

Formula 51

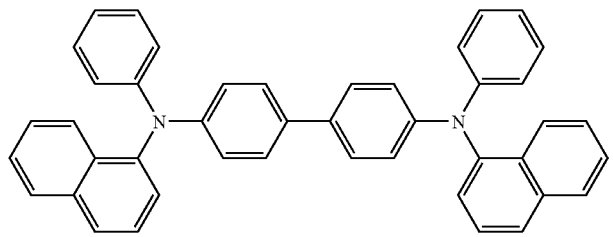

Formula 52

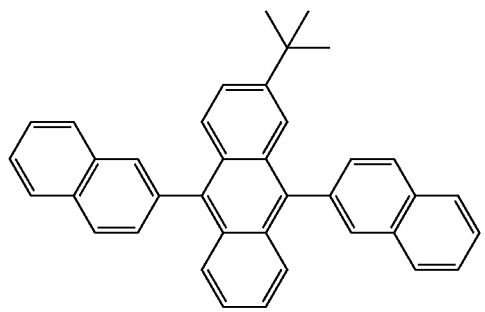

Formula 53

-continued

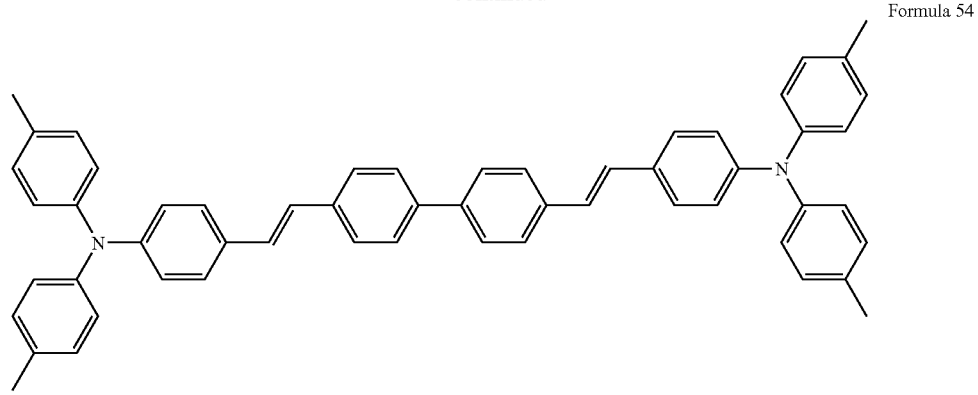

Formula 54

A 15 Ω/cm² (1000 Å) ITO glass substrate was cut to a size of 50 mm×50 mm×0.7 mm, microwave washed with acetone isopropyl alcohol for 15 minutes, microwave washed with pure water for 15 minutes, and washed with UV ozone for 30 minutes to prepare an anode. The compound of Formula 51 was vacuum deposited on the substrate to form a hole injection layer and the compound of Formula 52 was vacuum deposited thereon to form a hole transport layer. Then, the compounds of Formulas 53 and 54 were vacuum deposited in a weight ratio of 100:5 to form an emitting layer. Then, the compound of Formula 9 was vacuum deposited on the emitting layer to form an electron transport layer with a thickness of 250 Å. LiF was vacuum deposited on the electron transport layer to form an electron injection layer with a thickness of 6 Å, and Al was vacuum deposited on the electron injection layer to form a cathode with a thickness of 1500 Å. As a result, an organic light emitting device illustrated in FIG. 1A was manufactured. The obtained organic light emitting device had 20 cd/m² of blue light emitting at 6.1 V. Emitting efficiency and brightness half-life at 2000 nit were shown in Table 1.

EXAMPLES 11 TO 18

Manufacturing and Evaluating Organic Light Emitting Devices

Figure 3A:
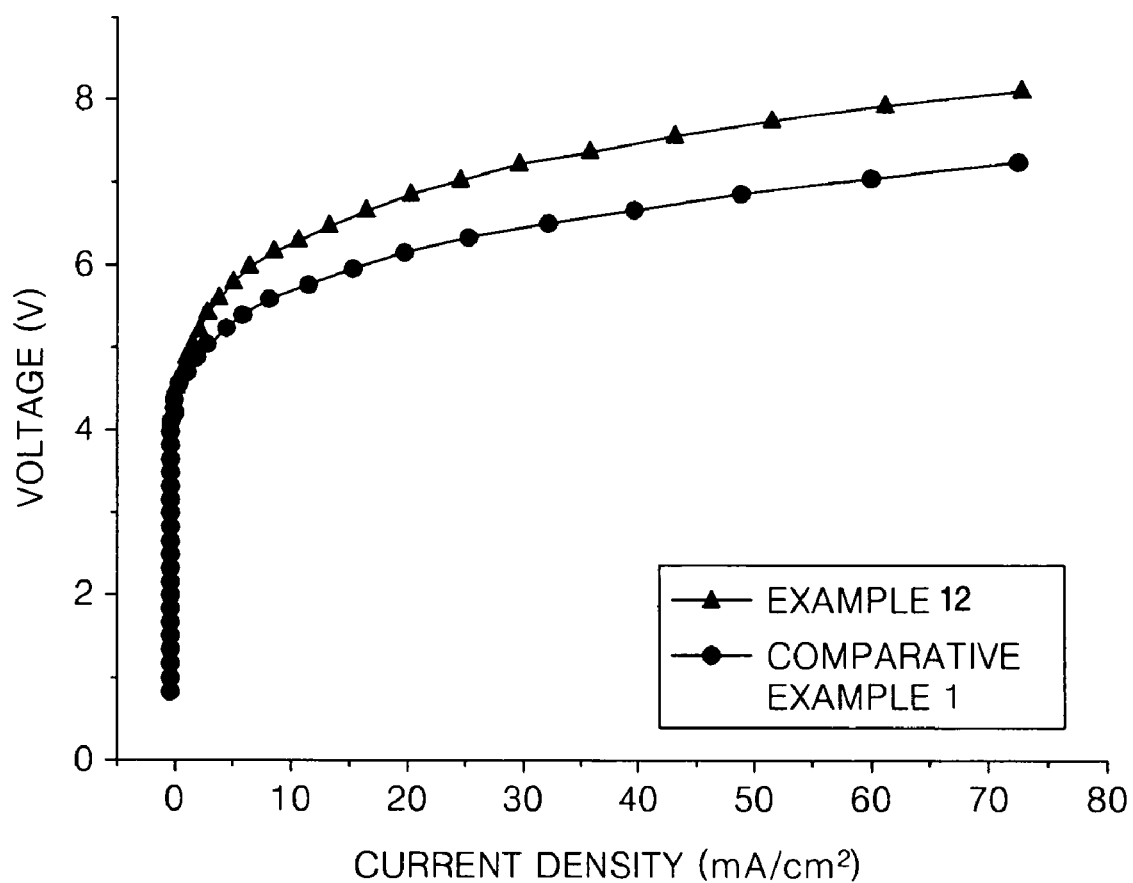
FIG. 3A is a graph illustrating current density-voltage characteristics of the organic light emitting devices prepared according to Example 12 and Comparative Example 1.
Figure 3B:
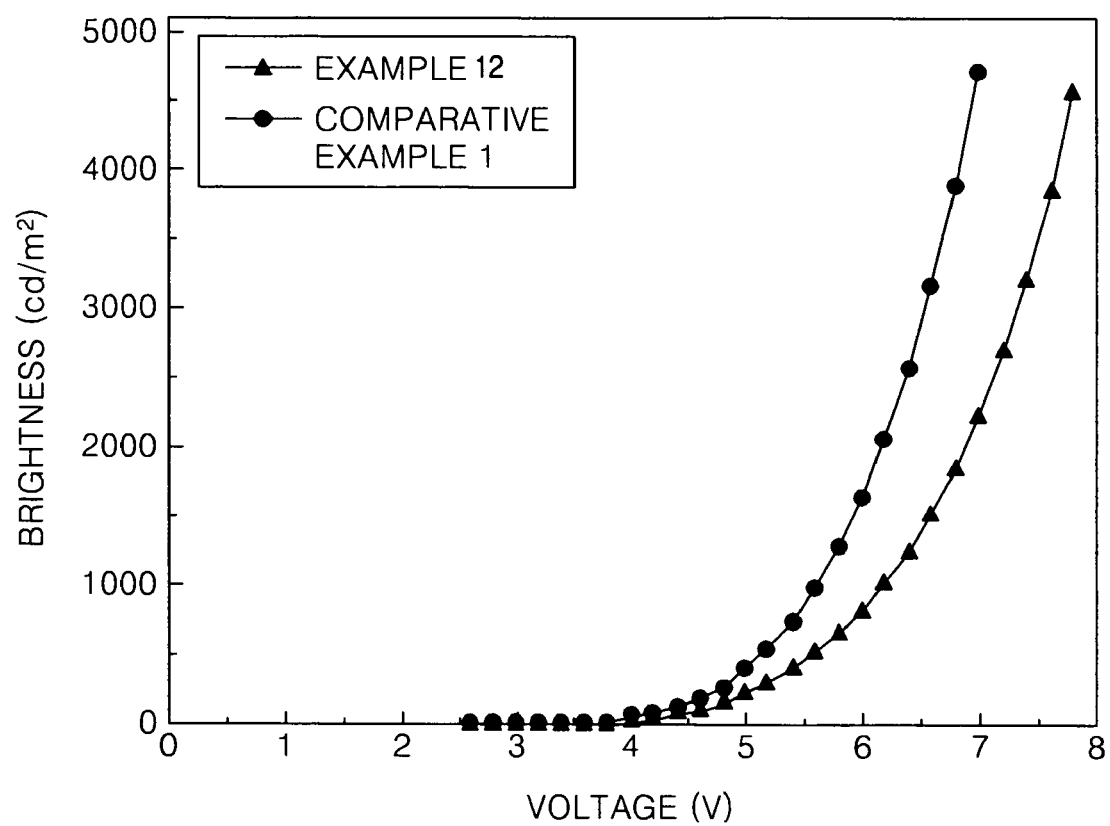
FIG. 3B is a graph illustrating voltage-brightness characteristics of the organic light emitting device prepared according to Example 12 and Comparative Example 1.

Organic light emitting devices were prepared in the same manner as in Example 10, except that compounds synthesized according to Examples 2 to 9 were respectively used instead of the compound of Formula 9 synthesized according to Example 1 as an electron transport layer. Driving voltage, emitting efficiency and brightness half-life at 2000 nit of the organic light emitting device were measured when the organic light emitting device is driven at a constant current of 20 mA/cm², and the results are shown in Table 1. In particular, FIG. 3A is a graph illustrating current density-voltage characteristics of the organic light emitting devices prepared according to Example 12 and Comparative Example 1, and FIG. 3B is a graph illustrating voltage-brightness characteristics of the organic light emitting devices prepared according to Example 12 and Comparative Example 1.

COMPARATIVE EXAMPLE 1

Manufacturing and Evaluating Organic Light Emitting Devices

An organic light emitting device was prepared in the same manner as in Example 10, except that Alq3 was used instead of the compound of Formula 9 synthesized according to Example 1 as an electron transport layer. Emitting efficiency, emitting color, brightness and lifetime of the organic light emitting device were measured, and the results are shown in Table 1. Driving voltage, emitting efficiency and brightness half-life at 2000 nit of the organic light emitting device were measured when the organic light emitting device is driven at a constant current of 20 mA/cm², and the results are shown in Table 1.

TABLE 1

|  | Compound | Driving voltage (V) | Emitting efficiency (cd/A) | Brightness half-life (hr) |
| --- | --- | --- | --- | --- |
| Example 10 | Example 1 | 6.1 | 6.8 | 1330 |
| Example 11 | Example 2 | 5.7 | 7.2 | 1280 |
| Example 12 | Example 3 | 5.8 | 7.3 | 1400 |
| Example 13 | Example 4 | 5.8 | 7.2 | 1350 |
| Example 14 | Example 5 | 5.7 | 7.2 | 1300 |
| Example 15 | Example 6 | 6.2 | 6.6 | 1310 |
| Example 16 | Example 7 | 5.6 | 6.7 | 1200 |
| Example 17 | Example 8 | 5.5 | 6.7 | 1220 |
| Example 18 | Example 9 | 5.4 | 6.9 | 1290 |
| Comparative Example 1 | Alq3 | 6.6 | 6.7 | 1240 |

It can be seen that the compound according to an embodiment of the present invention has low driving voltage and high emitting efficiency and has higher electron injecting and transporting capabilities compared to the compound used as an electron transport layer in Comparative Example 1. In addition, the organic light emitting devices employing the compounds of the present invention have excellent lifetime characteristics since the compounds of the present invention have high thermal stability due to a high glass transition temperature.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. An anthracene-based compound, represented by any one of Formulae 3 to 6 below:

(3)

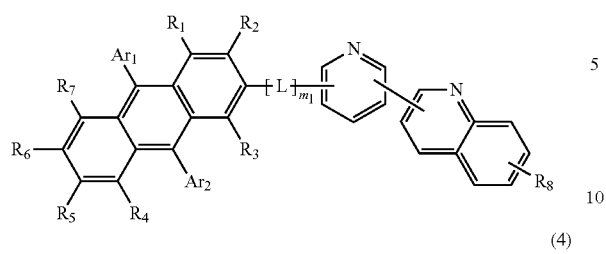

(4)

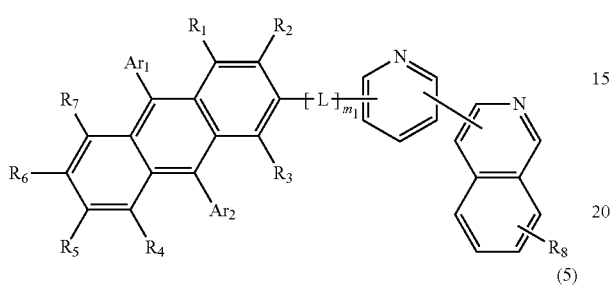

(5)

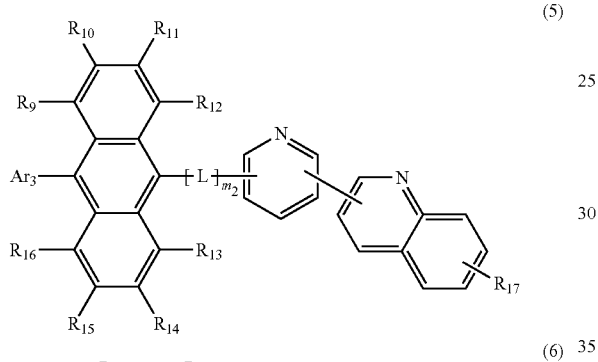

(6)

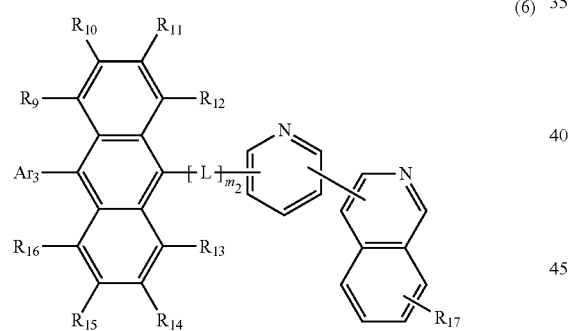

wherein $R_1$ to $R_{17}$ are identical to or different from each other and are each independently one selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group;

$Ar_1$, $Ar_2$ and $Ar_3$ are identical to or different from each other, and $Ar_1$, $Ar_2$ and $Ar_3$ are each independently a substituted or unsubstituted C6-C30 aryl group;

L is a substituted or unsubstituted C6-C30 arylene group or a substituted or unsubstituted C2-C30 heteroarylene group; and $m_1$ is an integer of 2 to 3, and $m_2$ is an integer of 1 to 3.

2. The anthracene-based compound of claim 1, wherein L is independently selected from the groups represented by formulae A-1 through A-21:

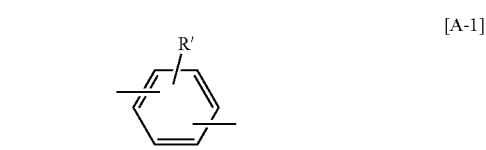 [A-1]

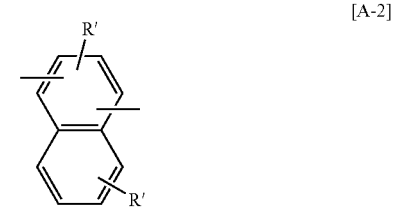 [A-2]

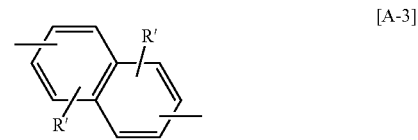 [A-3]

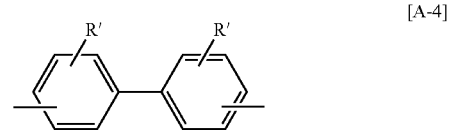 [A-4]

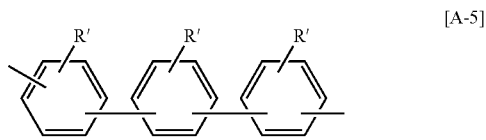 [A-5]

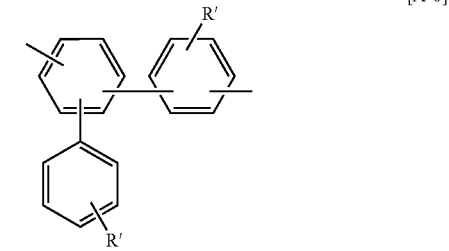 [A-6]

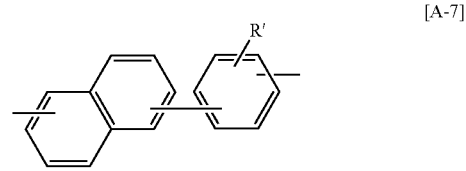 [A-7]

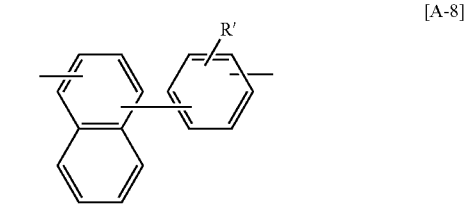 [A-8]

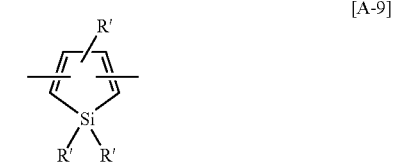 [A-9]

-continued

[A-10] 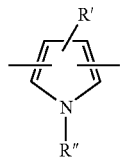

[A-11] 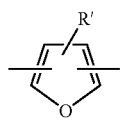

[A-12] 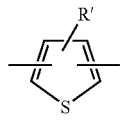

[A-13] 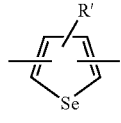

[A-14] 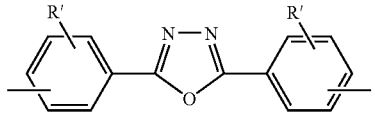

[A-15] 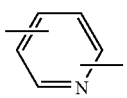

[A-16] 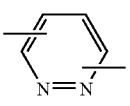

[A-17] 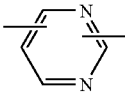

[A-18] 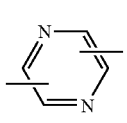

[A-19] 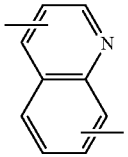

[A-20] 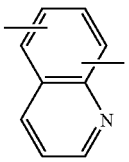

[A-21] 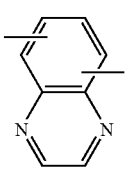

wherein R' is identical to or different from each other within the formulas and across formulas and is one selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group.

3. An anthracene-based compound of claim 1, wherein $Ar_1$, $Ar_2$ and $Ar_3$ are identical to or different from each other and are each independently represented by one of formulae B-1 through B-17:

[B-1] 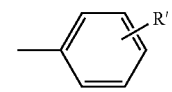

[B-2] 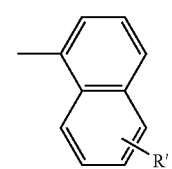

[B-3] 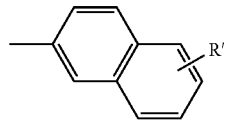

[B-4] 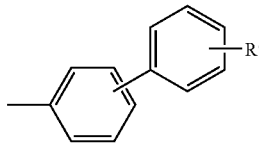

[B-5] 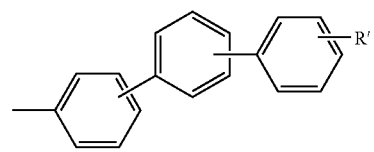

[B-6] 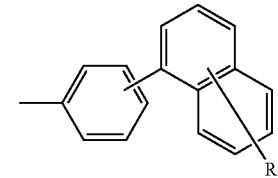

[B-7] 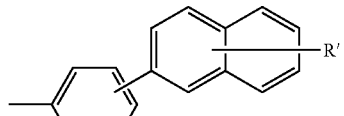

[B-8] 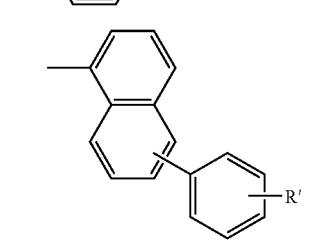

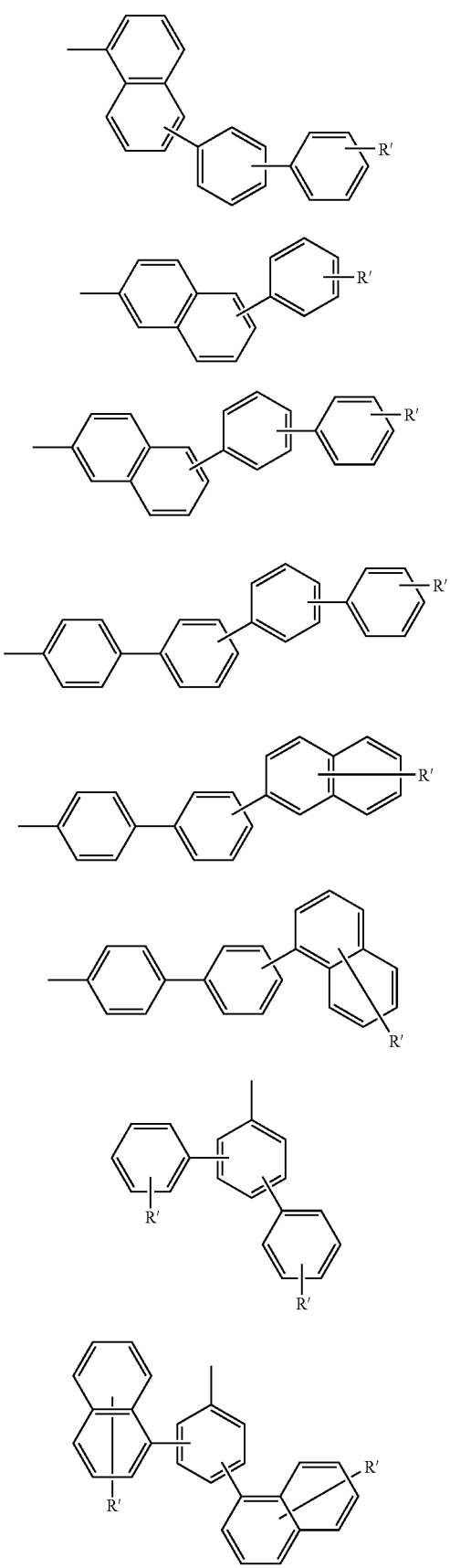

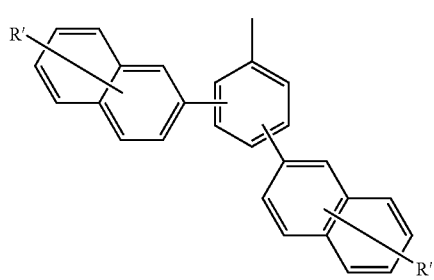

wherein R' is identical to or different from each other within the formulas and across formulas and is one selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group.

4. An anthracene-based compound of claim 1, wherein the compound is one of the compounds represented by Formulae 39-42 and 45-50 below:

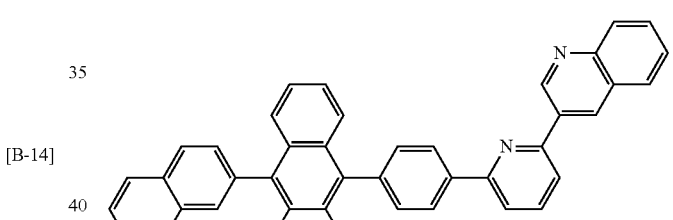

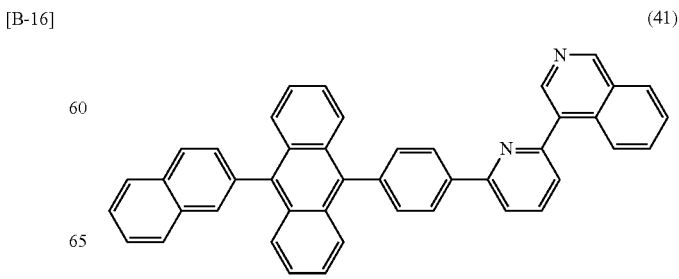

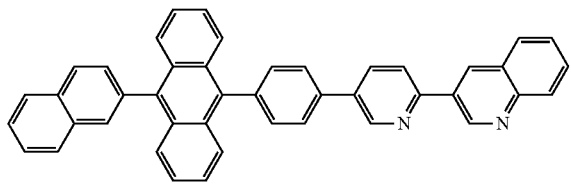
(42)
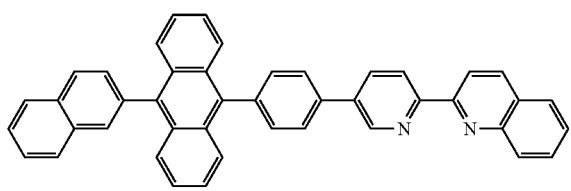
(45)
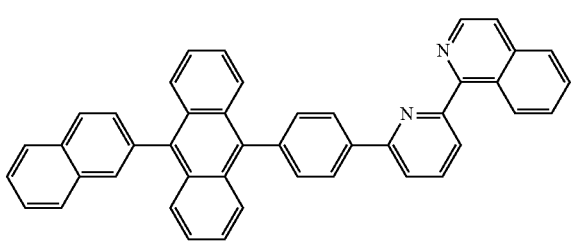
(46)
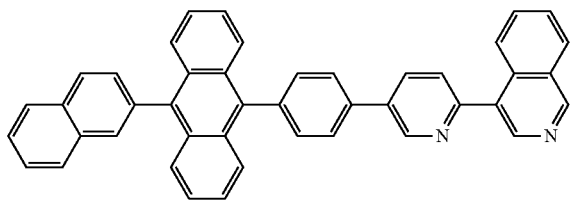
(47)
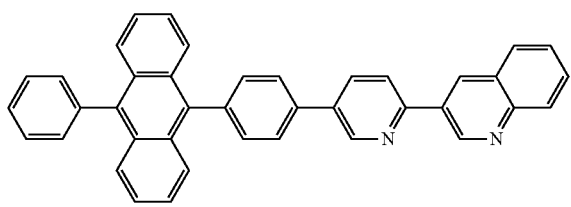
(48)
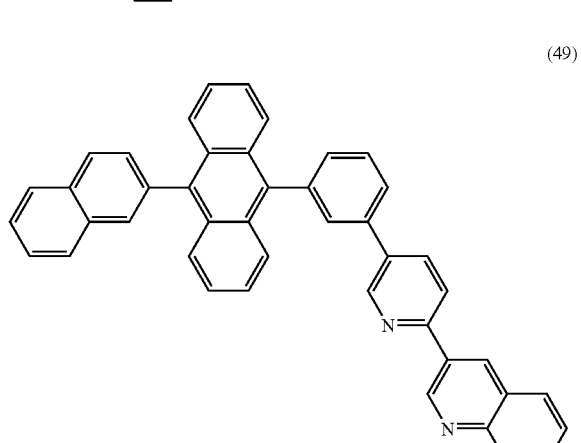
(49)
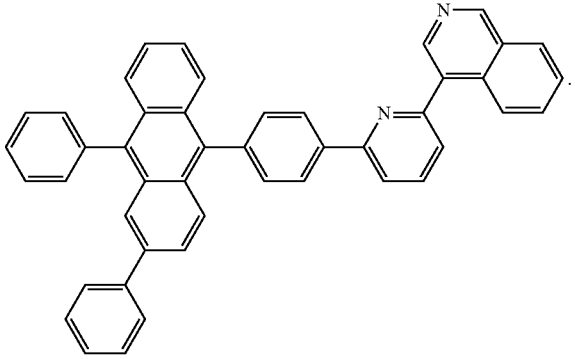
(50)
5. An anthracene-based compound represented by one of Formulae 3 to 6:
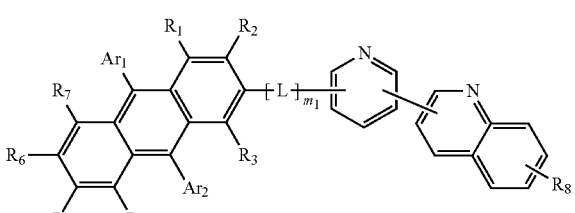
(3)
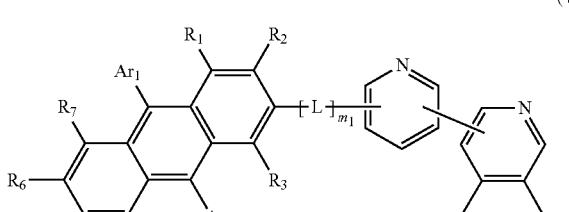
(4)
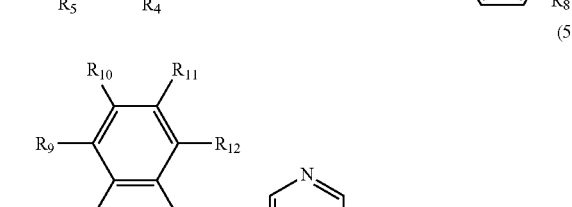
(5)
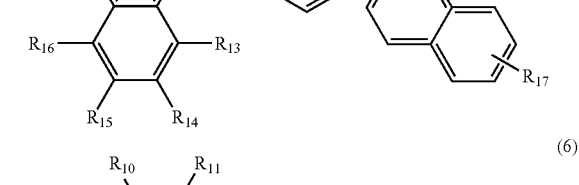
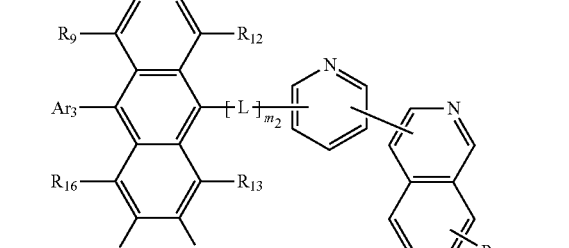
(6)

wherein $R_1$ to $R_{17}$ are identical to or different from each other and are each independently selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group;

$Ar_1$, $Ar_2$ and $Ar_3$ are each independently selected from the group consisting of Formulae B-1 through B-17:

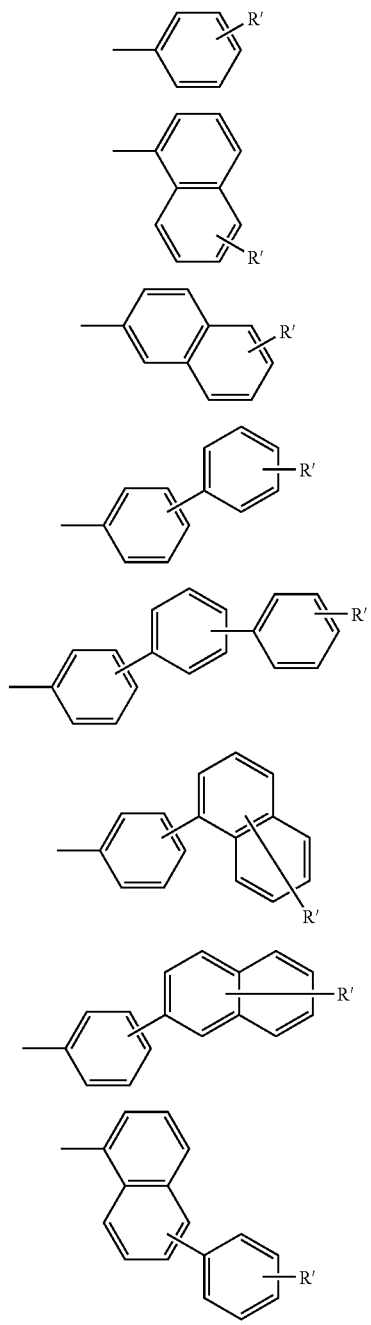

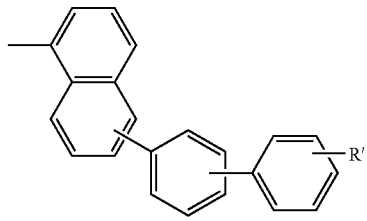

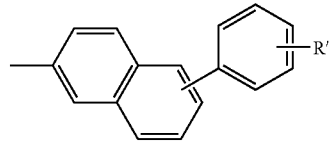

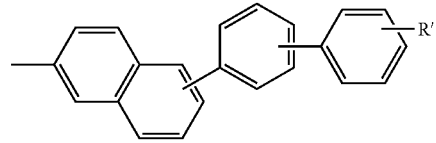

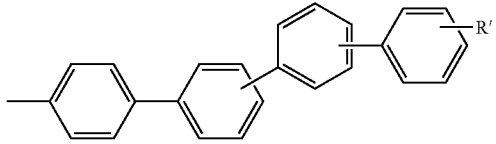

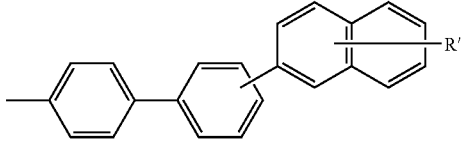

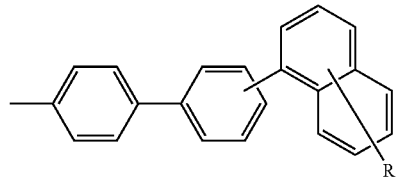

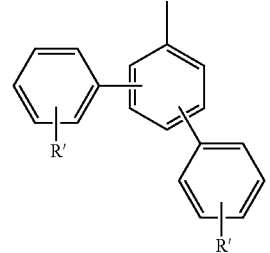

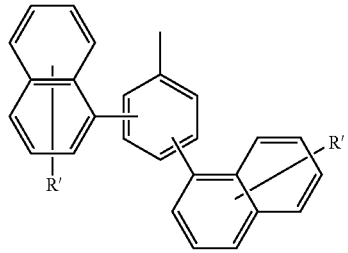

[B-17]
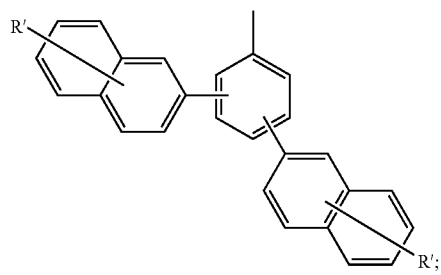
L is one of the groups represented by formulae A-1 through A-21:
[A-1]
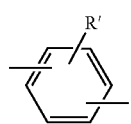
[A-2]
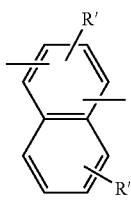
[A-3]
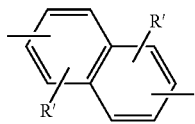
[A-4]
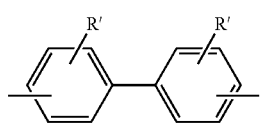
[A-5]
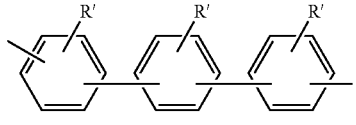
[A-6]
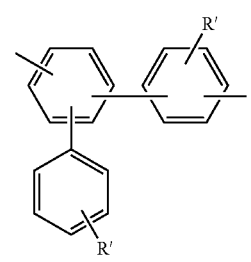
[A-7]
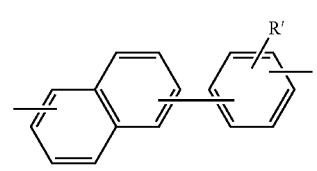
[A-8]
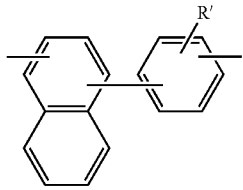
[A-9]
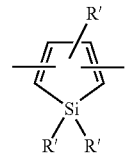
[A-10]
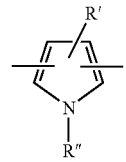
[A-11]
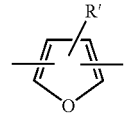
[A-12]
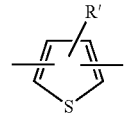
[A-13]
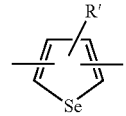
[A-14]
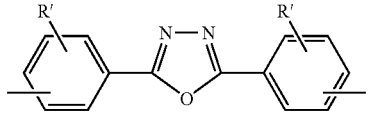
[A-15]
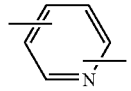
[A-16]
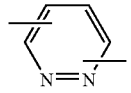
[A-17]
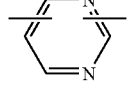
[A-18]
[A-19]
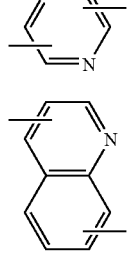

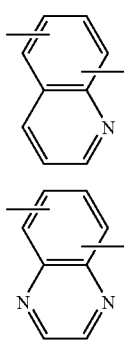

[A-20]

[A-21]

wherein R' is identical to or different from each other within the formulas and across formulas and is one selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group; and $m_1$ is an integer of 2 to 3, and $m_2$ is an integer of 1 to 3.

6. An organic light emitting device comprising a first electrode, a second electrode, and at least one organic layer between the first electrode and the second electrode, the organic layer comprising an anthracene-based compound of claim 5.

7. An organic light emitting device comprising:

a first electrode;

a second electrode; and at least one organic layer located between the first electrode and the second electrode, said at least one organic layer comprising an anthracene-based compound represented by any one of Formulae 3 to 6 below:

(3)

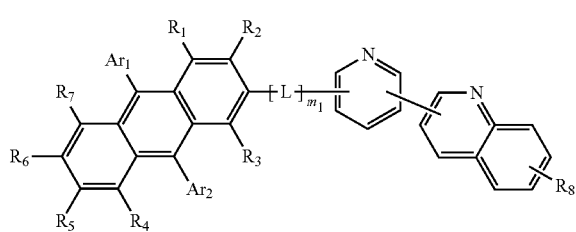

(4)

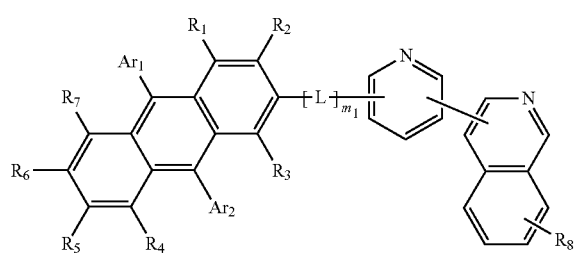

(5)

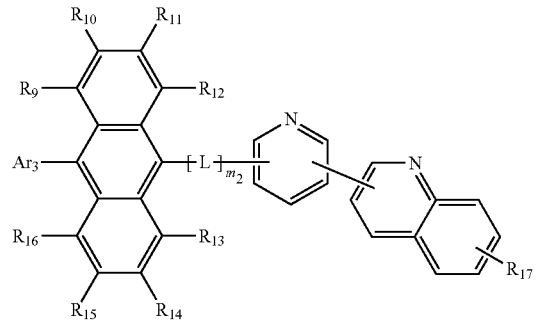

(6)

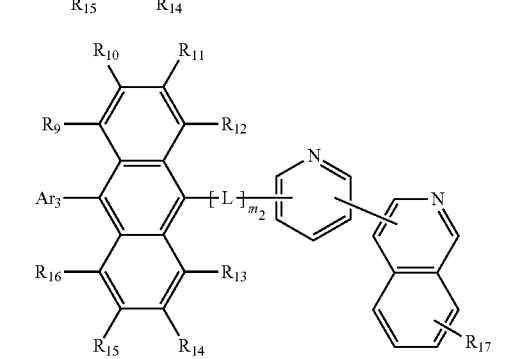

wherein $R_1$ to $R_{17}$ are identical to or different from each other and are each independently one selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group;

$Ar_1$, $Ar_2$ and $Ar_3$ are identical to or different from each other, and $Ar_1$, $Ar_2$ and $Ar_3$ are each independently a substituted or unsubstituted C6-C30 aryl group;

L is a substituted or unsubstituted C6-C30 arylene group or a substituted or unsubstituted C2-C30 heteroarylene group; and $m_1$ is an integer of 2 to 3, and $m_2$ is an integer of 1 to 3.

8. The organic light emitting device of claim 7, wherein the at least one organic layer comprising a compound represented by Formulae 3 to 6 is one selected from the group consisting of an emitting layer, a hole blocking layer, an electron transport layer and an electron injection layer.

9. The organic light emitting device of claim 7, wherein said at least one organic layer further comprises at least one layer selected from the group consisting of an emitting layer, a hole injection layer, a hole transport layer, an electron blocking layer, a hole blocking layer, an electron transport layer and an electron injection layer; located between the first electrode and the second electrode.

10. The organic light emitting device of claim 7, wherein the layer comprising a compound represented by Formulae 3 to 6 further comprises an organic metal complex.

11. The organic light emitting device of claim 7, wherein the layer comprising a compound represented by Formulae 3 to 6 further comprises an ionic salt.

12. The organic light emitting device of claim 7, wherein L is one of the groups represented by the formulae below:
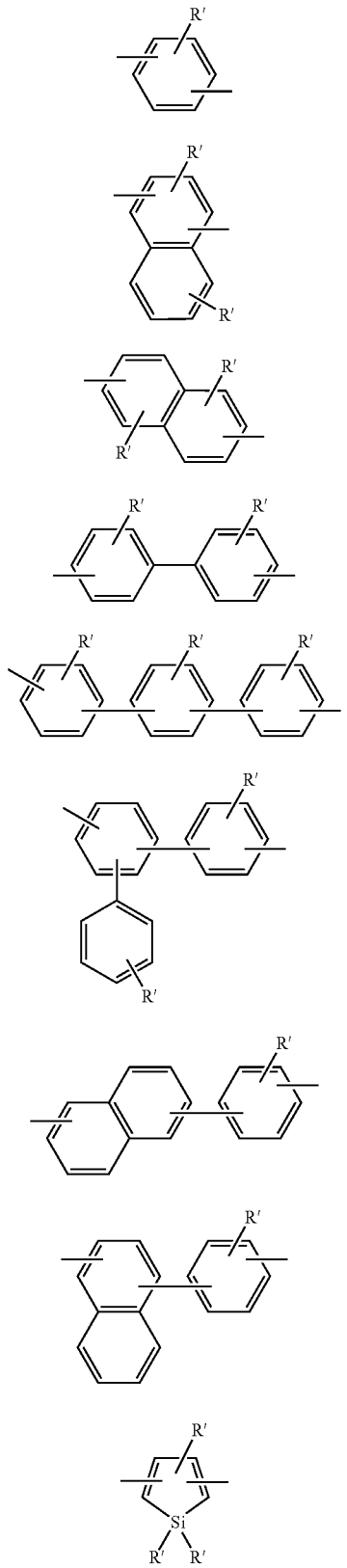
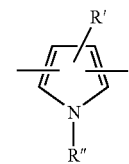
[A-10]
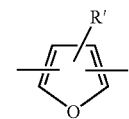
[A-11]
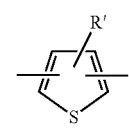
[A-12]
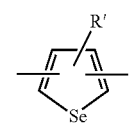
[A-13]
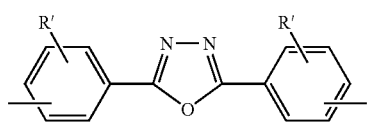
[A-14]
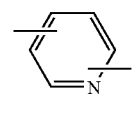
[A-15]
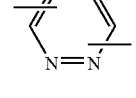
[A-16]
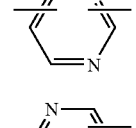
[A-17]
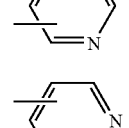
[A-18]
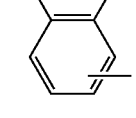
[A-19]
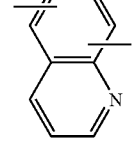
[A-20]
[A-21]

wherein R' is identical to or different from each other within the formulas and across formula and is one selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group.

13. The organic light emitting device of claim 7, wherein Ar$_1$, Ar$_2$ and Ar$_3$ are identical to or different from each other and are each independently represented by one of formulae B-1 through B-17:

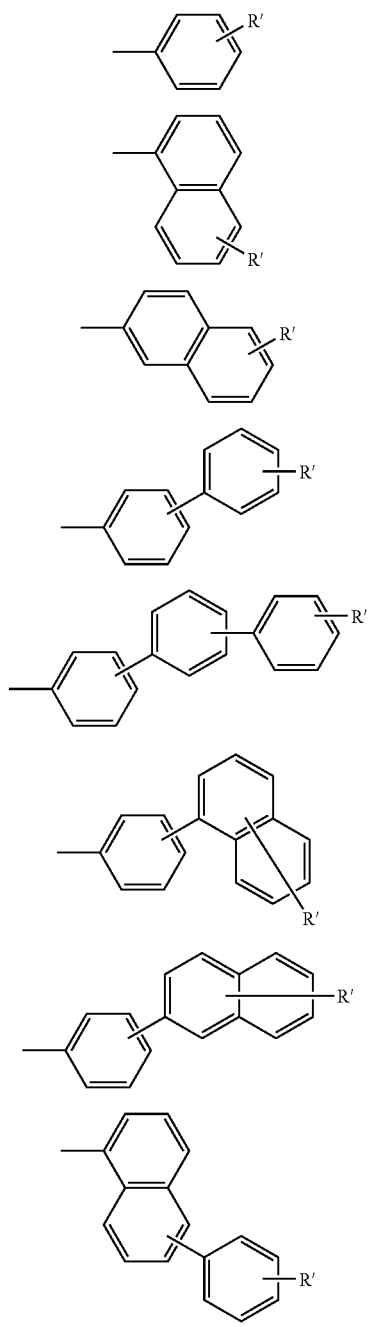
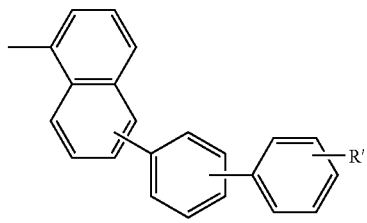
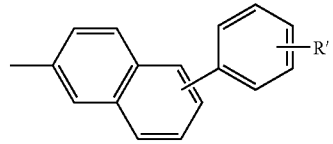
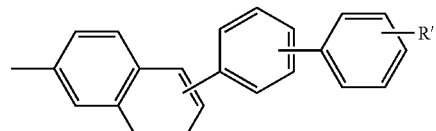
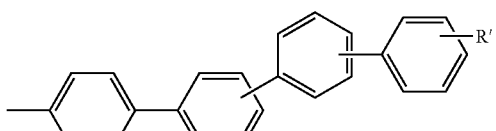
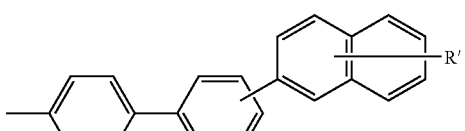
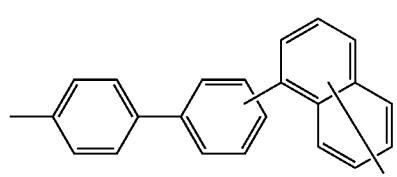
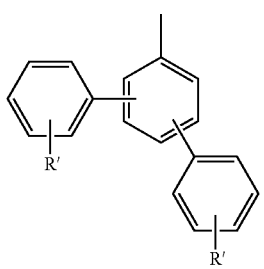
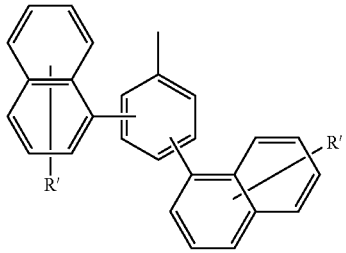

[B-17]

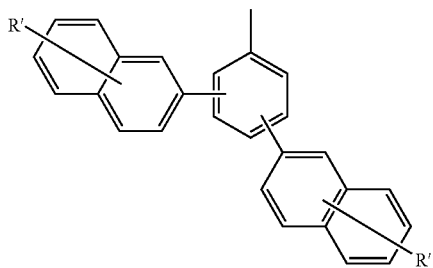

wherein R' is identical to or different from each other within the formulas and across formulas and is one selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group.

14. The organic light emitting device of claim 7, wherein the anthracene-based compound is one of the compounds represented by Formulae 39-42 and 45-50:

(39)

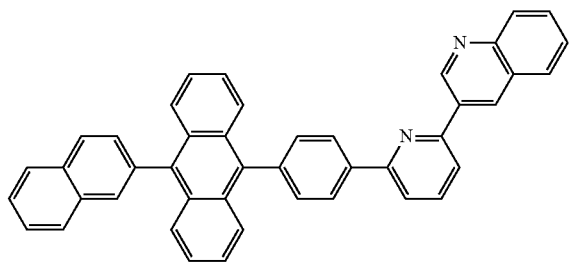

(40)

(41)

(42)

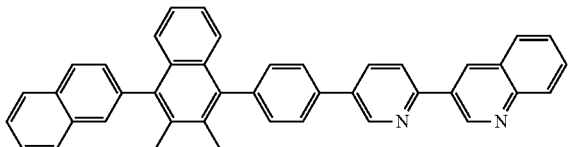

(45)

(46)

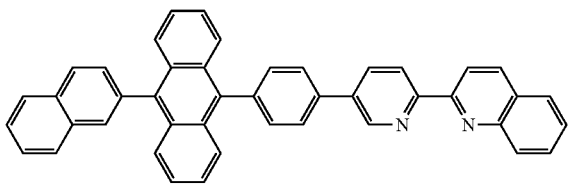

(47)

(48)

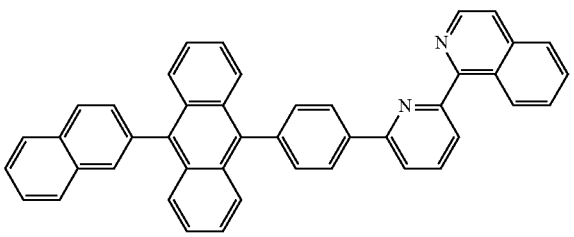

(49)

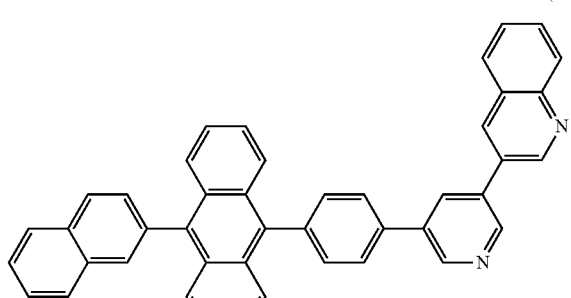

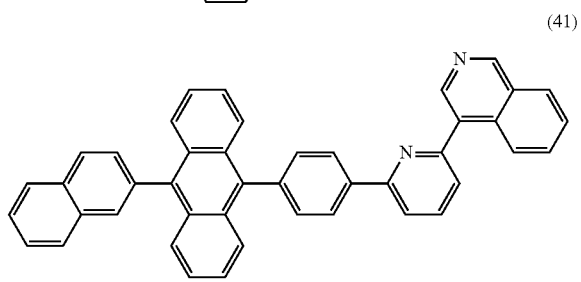

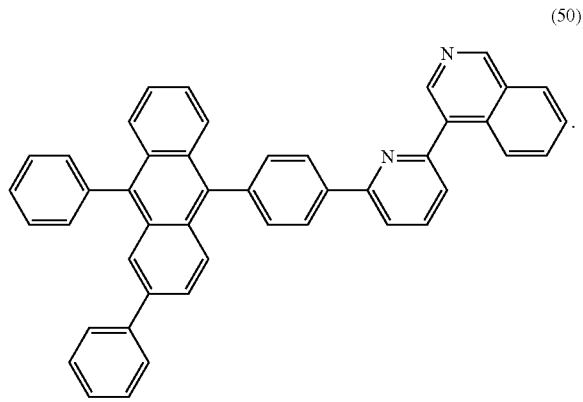

(50)

15. An anthracene-based compound represented by one of Formula 51 or Formula 52:

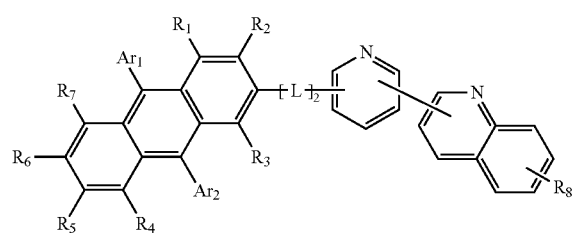

(51)

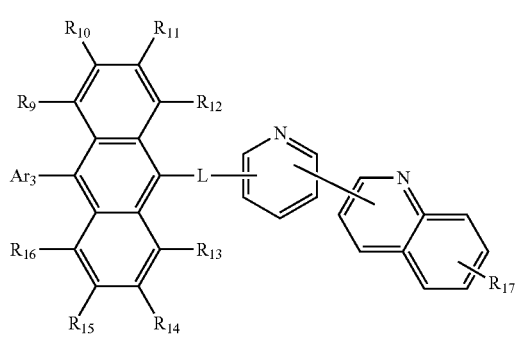

(52)

wherein $R_1$ to $R_{17}$ are identical to or different from each other and are each independently one selected from the group consisting of a hydrogen atom, a halogen atom, a cyano group, a hydroxyl group, a substituted or unsubstituted. C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group;

$Ar_1$, $Ar_2$ and $Ar_3$ are identical to or different from each other, and $Ar_1$, $Ar_2$ and $Ar_3$ are each independently a substituted or unsubstituted C6-C30 aryl group;

L is a substituted or unsubstituted C6-C30 arylene group or a substituted or unsubstituted C2-C30 heteroarylene group.

16. An organic light emitting device comprising a first electrode, a second electrode, and at least one organic layer between the first electrode and the second electrode, the organic layer comprising an anthracene-based compound of claim 15.

* * * * *